United States Patent
Endo et al.

(10) Patent No.: US 10,791,718 B2
(45) Date of Patent: Oct. 6, 2020

(54) METHOD OF MAINTAINING OVARIES OF MARINE FISH, METHOD OF ADJUSTING CULTURE SOLUTION, AND METHOD OF PRODUCING EGGS OR FERTILIZED EGGS OF MARINE FISH

(71) Applicant: Nippon Suisan Kaisha, Ltd., Minato-ku (JP)

(72) Inventors: Taku Endo, Saiki (JP); Naoki Kumakura, Saiki (JP); Shinji Adachi, Hakodate (JP)

(73) Assignee: Nippon Suisan Kaisha, Ltd., Tokyo (JP)

( * ) Notice: Subject to any disclaimer, the term of this patent is extended or adjusted under 35 U.S.C. 154(b) by 324 days.

(21) Appl. No.: 15/561,378

(22) PCT Filed: Jan. 19, 2016

(86) PCT No.: PCT/JP2016/051465
§ 371 (c)(1),
(2) Date: Sep. 25, 2017

(87) PCT Pub. No.: WO2016/152215
PCT Pub. Date: Sep. 29, 2016

(65) Prior Publication Data
US 2018/0077909 A1 Mar. 22, 2018

(30) Foreign Application Priority Data
Mar. 26, 2015 (JP) .................................. 2015-065124

(51) Int. Cl.
*A01K 61/10* (2017.01)
*A01K 67/02* (2006.01)
*A01N 1/02* (2006.01)

(52) U.S. Cl.
CPC .............. *A01K 61/10* (2017.01); *A01K 67/02* (2013.01); *A01N 1/0205* (2013.01); *A01N 1/0226* (2013.01); *Y02A 40/81* (2018.01); *Y02A 40/812* (2018.01)

(58) Field of Classification Search
CPC ...... A01K 61/10; A01K 67/02; A01N 1/0226; A01N 1/0205
See application file for complete search history.

(56) References Cited

U.S. PATENT DOCUMENTS

| | | | |
|---|---|---|---|
| 2004/0053407 A1 | 3/2004 | Cortvrindt et al. | |
| 2008/0134983 A1* | 6/2008 | Binkowski | A01K 61/95 119/217 |
| 2010/0303952 A1* | 12/2010 | Bahmani | A01K 67/02 426/2 |
| 2010/0313819 A1* | 12/2010 | Onozato | A01K 67/00 119/215 |
| 2011/0132271 A1* | 6/2011 | Slembrouck | A01K 67/02 119/218 |
| 2017/0142941 A1* | 5/2017 | Luo | A01K 61/95 |
| 2018/0035652 A1* | 2/2018 | Yoshizaki | A01K 67/027 |

FOREIGN PATENT DOCUMENTS

| | | |
|---|---|---|
| JP | 7-224090 A | 8/1995 |
| JP | 2004-514458 A | 5/2004 |
| JP | 2007-222150 A | 9/2007 |

OTHER PUBLICATIONS

European Office Action dated May 9, 2019, in Patent Application No. 16 768 118.8, 6 pages.
Patiño, R. et al., "Effects of external pH on hormonally regulated ovarian follicle maturation and ovulation in Atlantic croacker", General and Comparative Endocrinology, XP027185084, vol. 141, No. 2, Apr. 1, 2005, pp. 126-134.
International Search Report dated Apr. 19, 2016, in PCT/JP2016/051465, filed Jan. 19, 2016.
Mylonas et al., "Preparation and Administration of Gonadotropin-Releasing Hormone Agonist (GnRHa) Implants for the Artificial Control of Reproductive Maturation in Captive-Reared Atlantic Bluefin Tuna (*Thunnus thynnus thynnus*)", Reviews in Fisheries Science, vol. 15, Issue 3, 2007, p. 183-210.
Endo et al., "Production of fertilized eggs by artificial insemination from harvested Pacific Bluefin tuna (*Thunnus orientalis*)", Abstracts of the annual meeting of the Japanese Society of Fisheries Science, 2012, p. 130, with English translation.
Abe et al., "Development of an in vitro culture system for producing eel larvae from immature ovarian follicles in Japanese eel *Anguilla japonice*". Fisheries Science, vol. 76, p. 257-265.
Tsai et al., "Development of in vitro culture method for early stage zebrafish (*Danio rerio*) ovarian follicles for use in cryopreservation studies". Theriogenology, vol. 74, 2010, p. 290-303.
Ogiwara et al., "A New In Vitro Ovulation Model for Medaka Based on Whole Ovary Culture", Zoological Science, vol. 27, 2010, p. 762-767.
Extended European Search Report dated Jul. 27, 2018 in Patent Application No. 16768118.8, 7 pages.

(Continued)

*Primary Examiner* — Trinh T Nguyen
(74) *Attorney, Agent, or Firm* — Oblon, McClelland, Maier & Neustadt, L.L.P.

(57) ABSTRACT

Provided are a method of maintaining the ovaries of marine fish, and a method of obtaining fertilized egg. Provided is a method of maintaining ovaries in which the ovaries are removed from marine fish and the ovaries or fragmented ovaries are cultured in a culture solution. Also, provided is a method of obtaining fertilized eggs of marine fish, the method including allowing ovaries, which have been maintained after removal to ovulate and performing artificial insemination. Further, the present invention relates to a method of maintaining the fertilization capability of ovulated eggs of marine fish by using the culture solution. According to the present invention, fertilized eggs of marine fish can be easily obtained and seed can be efficiently produced.

22 Claims, 8 Drawing Sheets

(56) References Cited

OTHER PUBLICATIONS

Skoblina, M.N. et al., "Stimulation of in vitro Oocyte Ovulation by Progesterone and Homologous Pituitary Gonadotropic Hormone in Sturgeons" Russian Journal of Developmental Biology, vol. 43, No. 3, XP035055556, 2012, pp. 157-163.
Goetz, F. W. et al., "Effects of pH on In Vitro Ovulation of Goldfish (*Carassius auratus*) Oocytes" The Journal of Experimental Zoology, vol. 235, No. 1, XP055493886, 1985, pp. 81-85.

* cited by examiner

FIG. 7A
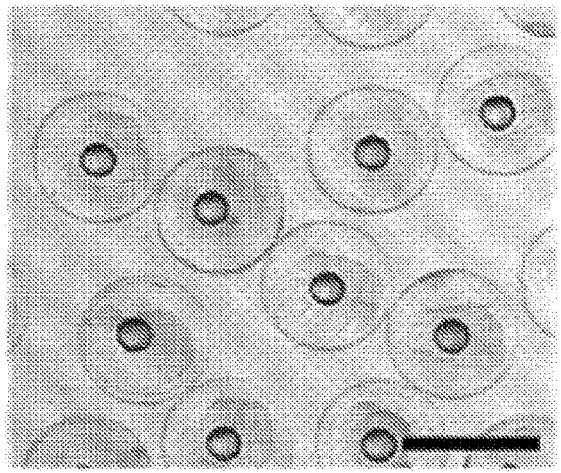
FIG. 7B
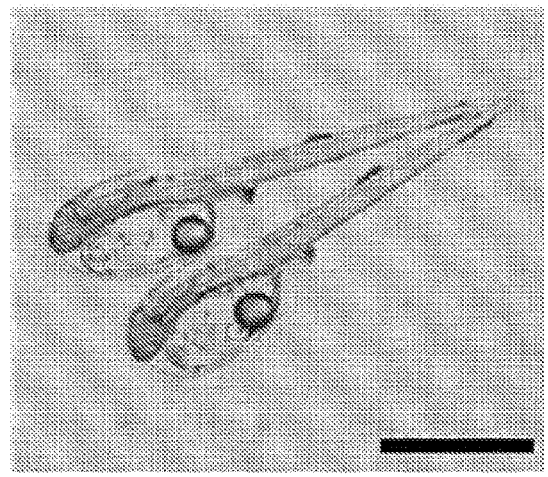
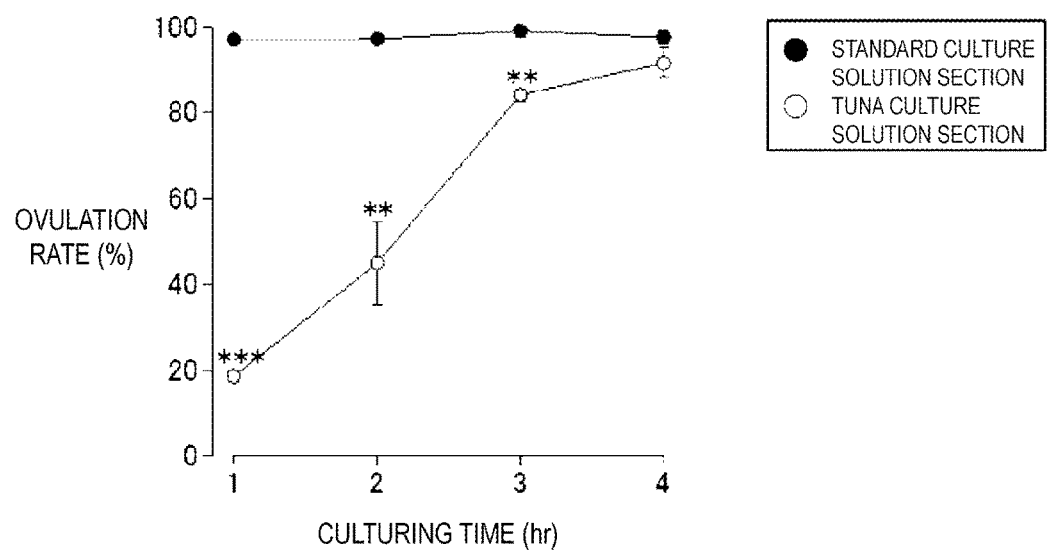
FIG. 8

METHOD OF MAINTAINING OVARIES OF MARINE FISH, METHOD OF ADJUSTING CULTURE SOLUTION, AND METHOD OF PRODUCING EGGS OR FERTILIZED EGGS OF MARINE FISH

PRIORITY RIGHTS

This international patent application claims priority based on JP-A-2015-65124, which is a patent application filed with the Japan Patent Office on Mar. 26, 2015. All contents of JP-A-2015-65124 are incorporated herein by reference.

TECHNICAL FIELD

The present invention relates to a method of maintaining ovaries of marine fish, a method of adjusting a culture solution, and a method of producing eggs or fertilized eggs of marine fish.

BACKGROUND ART

Collecting eggs naturally spawned by natural or farmed fish has been employed as a method of producing eggs from marine fish. In some farmed fish, a gonadotropin-releasing hormone is administered to fish swimming in water to induce maturation and spawning (Non-patent Document 1). However, it is difficult to collect eggs obtained by the above method without damage, and the success rate of artificial insemination is often low.

Furthermore, there is a method of obtaining matured fertilizable eggs and sperm from fish caught by fishing and artificially inseminating them (Non-patent Document 2). To ensure successful artificial insemination, eggs must be obtained from an individual having eggs in a phase suitable for fertilization, for example, eggs that have been ovulated. In the lifecycle of marine fish, however, the duration for which a fish possesses eggs in a phase suitable for fertilization is short. Furthermore, in marine fish, it is difficult to visually distinguish individuals that have eggs in a phase suitable for fertilization. When the status of eggs is examined after a fish is caught, the fish ends up debilitated or dead due to the examination, and therefore it is difficult to catch a fish, examine the state of eggs of that fish, and then return it to the water and wait until the eggs are in a phase suitable for fertilization. For this reason, the success rate of artificial fertilization in eggs obtained by the above method is low. Furthermore, when ovaries are removed from caught fish, it is difficult to obtain fertilizable eggs from the removed ovaries because the eggs quickly become inactive.

PRIOR ART DOCUMENTS

Non-Patent Documents

Non-patent Document 1: C. C. Mylonas et al., Reviews in Fisheries Science, Volume 15, Issue 3, pp. 183-210 (2007)

Non-patent Document 2: Endo et al., Abstracts of the annual meeting of the Japanese Society of Fisheries Science, 2012: 130

SUMMARY OF INVENTION

Technical Problem

The present invention relates to maintaining fertilization capability of eggs contained in removed ovaries and obtaining eggs from the ovaries of marine fish, and particularly relates to obtaining eggs having the capability of being fertilized and hatched.

Solution to Problem

The present invention relates to the inventions below.

1. A method of maintaining ovaries of marine fish, the method including removing ovaries from marine fish, and culturing the removed ovaries or fragmented ovaries in a culture solution.
2. The method according to 1, wherein eggs contained in the ovaries are maintained in a fertilizable state.
3. The method according to 1 or 2, wherein the ovaries are ovaries containing oocytes.
4. The method according to any one of 1 to 3, wherein a pH of the culture solution is adjusted to within a range from +0.5 to −0.5 relative to a pH of ovarian cavity fluid of the fish from which the ovaries have been removed.
5. The method according to any one of 1 to 4, wherein an osmotic pressure of the culture solution is not less than 100 mOsm/kg and not greater than 6000 mOsm/kg.
6. The method according to any one of 1 to 5, wherein the culture solution contains at least one type selected from sodium ions, potassium ions, calcium ions, and magnesium ions.
7. The method according to 6, wherein a sodium ion concentration of the culture solution is not less than 120 mM and not greater than 250 mM.
8. The method according to 6 or 7, wherein a potassium ion concentration of the culture solution is not less than 5 mM and not greater than 10 mM.
9. The method according to any one of 6 to 8, wherein a calcium ion concentration of the culture solution is not less than 1.5 mM and not greater than 5.0 mM.
10. The method according to any one of 6 to 9, wherein a magnesium ion concentration of the culture solution is not less than 1.0 mM and not greater than 2.0 mM.
11. The method according to any one of 1 to 10, wherein the culture solution contains at least one of chloride ions and sulfate ions.
12. The method according to any one of 1 to 11, wherein the culture solution contains at least one type selected from glucose, galactose, fructose, and sucrose.
13. The method according to any one of 1 to 12, wherein the culture solution contains an antibiotic.
14. The method according to any one of 1 to 13, wherein the target marine fish for ovarian removal is a farmed fish.
15. The method according to any one of 1 to 13, wherein the target marine fish for ovarian removal is fish caught by fishing.
16. The method according to any one of 1 to 15, wherein the marine fish is a fish of the Scombridae family.
17. A method of producing eggs of marine fish, the method including obtaining eggs by causing ovaries cultured by the method described in any one of 1 to 16 to ovulate.
18. A method of producing fertilized eggs of marine fish, the method including obtaining fertilized eggs by cross-fertilizing eggs obtained by the method described in 17 and sperm.
19. Eggs of marine fish, the eggs being obtained by the method described in 17.
20. Fertilized eggs of marine fish, the eggs being obtained by the method described in 18.

21 A method of rearing marine fish, the method including rearing larvae hatched from fertilized eggs obtained by the method described in 18 to young fry, immature fish, or adult fish.

22 A method of producing farmed marine fish, the method including rearing larvae hatched from fertilized eggs obtained by the method described in 18 to young fry, immature fish, or adult fish.

23 A method of adjusting a culture solution used for maintaining ovaries or fragmented ovaries removed from marine fish, the method including: measuring a pH of ovarian cavity fluid of a fish species that is a target of ovarian removal; and adjusting a pH of the culture solution to within a range from +0.5 to −0.5 relative to a measured pH of ovarian cavity fluid of a fish that is a target of ovarian removal by adjusting a concentration of at least one type selected from sodium ions, potassium ions, calcium ions, and magnesium ions.

24 The method according to 23, wherein molar concentrations of sodium ions, potassium ions, calcium ions, and magnesium ions in the culture solution are adjusted to molar concentrations from ¼ to 4 times the respective molar concentrations of sodium ions, potassium ions, calcium ions, and magnesium ions in blood serum of the marine fish used in ovarian removal.

Advantageous Effects of Invention

The present invention makes it possible to maintain removed ovaries or fragmented ovaries of marine fish in a fertilizable state. Furthermore, the present invention makes it possible to obtain eggs from the above ovaries, and particularly to obtain eggs having the capability of being fertilized and hatched. For this reason, fertilized eggs of marine fish can be easily obtained and seed can be efficiently produced.

BRIEF DESCRIPTION OF DRAWINGS

FIG. 5 shows photographs illustrating the forms of ovulated eggs 2 hours after fragmentation and microplate distribution treatment in each experimental section.

FIG. 7 shows photographs of fertilized eggs and hatched larvae obtained from ovulation ex vivo. FIG. 7A shows fertilized eggs, and FIG. 7B shows hatched larvae.

FIG. 8 is a graph showing ovulation rate versus culturing time of the standard culture solution section in which the culture solution described in Example 1 is used in a test using ovaries of a first individual, or a tuna culture solution section in which a culture solution matching the metal ion composition of tuna blood serum is used. In the graph, the asterisks indicate a significant difference relative to the standard culture solution section, wherein * means $P<0.05$,  means $P<0.01$, and * means $P<0.001$.

DESCRIPTION OF EMBODIMENTS

Figure 1:
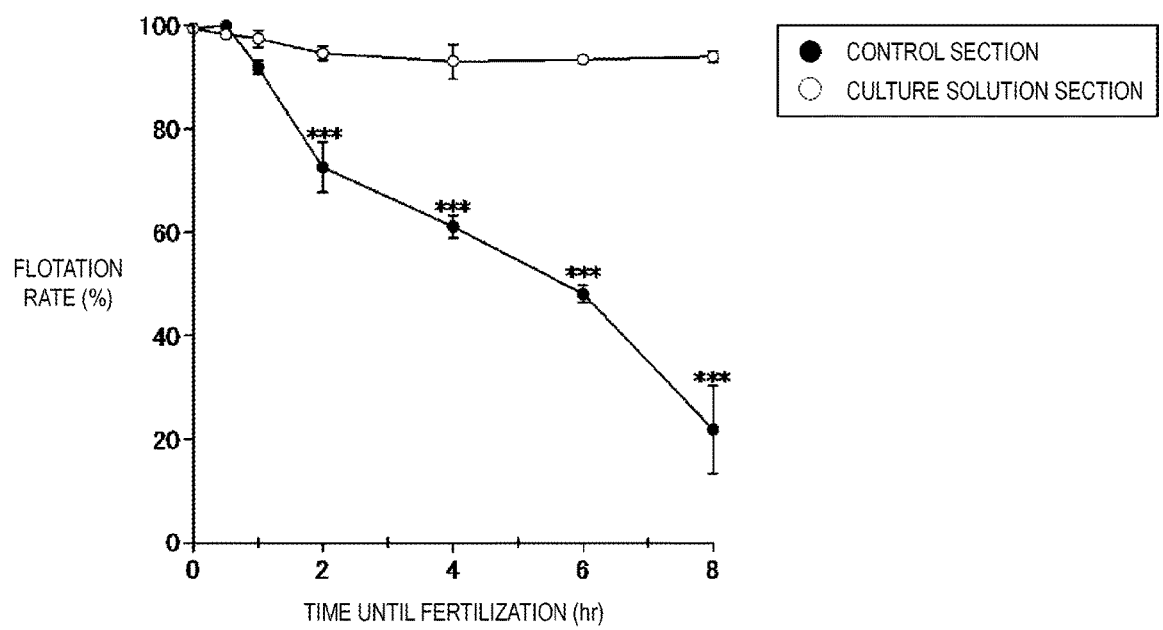
FIG. 1 is a graph showing flotation rate versus fertilization time in the control section in which eggs ovulated in vivo are untreated and in the culture solution section in which eggs are immersed in culture solution. The asterisks indicate a significant difference relative to 0 hours, wherein * means $P<0.05$,  means $P<0.01$, and * means $P<0.001$.

Embodiments and the like of the present invention will be described in detail below, but the present invention is not limited to the below embodiments and the like, and optional modifications may be made within a scope that does not deviate from the essence of the present invention. Note that in the present specification, "from A to B" or "A to B" are used as expressions that include the starting and ending numerical values or physical quantities. Furthermore, in the present specification, "at least one of A and B" means "one or both of A and B." That is, "at least one of A and B" includes "A only," "B only," and "both A and B."

The present invention relates to a method of maintaining ovaries of marine fish, the method including removing ovaries from marine fish, culturing the removed ovaries or fragmented ovaries in a culture solution, and maintaining the eggs contained in the ovaries in a fertilizable state (also referred to as "method of maintaining ovaries of the present invention" hereinafter).

Another embodiment of the present invention is a method of producing eggs of marine fish, the method including obtaining eggs by causing the ovaries cultured by the method of maintaining ovaries of the present invention to ovulate (method of producing eggs of the present invention).

Yet another embodiment of the present invention is a method of producing fertilized eggs of marine fish, the method including obtaining fertilized eggs by cross-fertilizing eggs obtained by the method of producing eggs of marine fish of the present invention and sperm (method of producing fertilized eggs of the present invention).

Further embodiments of the present invention are a method of rearing marine fish (method of rearing marine fish of the present invention) and a method of producing farmed marine fish (method of rearing marine fish of the present invention), which are associated with the method of producing eggs of the present invention.

Note that all embodiments of the present invention are also collectively referred to as "the present invention" hereinafter.

In the present specification, the term "marine fish" means fish that inhabit the ocean in the natural environment, and includes fish that become adult fish and fish that mature eggs in the ocean, fish that ovulate in the ocean, and fish that fertilize in the ocean.

Fish include bony fish species. Bony fish include fish of the Clupeiformes order, Aulopiforms' order, Myctophiformes order, Lampriformes order, Polymixiiformes order, Gasiform order, Lophiiformes order, Mugiliformes order, Atheriniformes order, Beloniformes order, Beryciformes order, Zeiformes order, Scorpaeniformes order, Perciform's order, Pleuronectiformes order, and Tetraodontiformes order. Fish of the perciforms order include fish of the Percoidei suborder, Coracoidal suborder, Trachinoidei suborder, Gobioidei suborder, Acanthuroidei suborder, Scombroidei suborder, and Stromateoidei suborder.

Fish of the Scombroidei suborder include fish of the Sphyraenidae family, Gempylidae family, Trichiuridae family, Scombridae family, Xiphiidae family, and Istiophoridae family. Fish include farmed fish. Fish include artificially bred fish. Fish include crossbred fish in addition to fish of specified species. Fish include artificially produced polyploidized fish including diploid, triploid, tetraploid, and ameuploid fish. Fish include artificially produced chimera fish, transgenic individuals, genetically modified individuals, genetically recombined individuals, and transformed fish.

In the present specification, the term "farmed fish" means fish that are artificially bred in fish cages. Farmed fish include fish bred particularly with the object of aquaculture.

In the present specification, the term "ovaries" means organs that produce eggs in the female reproductive organs. Ovaries include not only those produced in the natural environment, but also those produced in an artificial environment. Ovaries include those produced in vivo. Ovaries include those matured by administration of sex hormones, exemplified by gonadotropin-releasing hormone, being administered to fish.

In the present specification, the term "eggs" means female gametes produced in the ovaries. Eggs include those in which oocytes have matured. Eggs include unfertilized eggs before fertilization and fertilized eggs that were fertilized in the natural environment or an artificial environment.

In the present specification, the term "oocytes" means female reproductive cells produced by meiosis. Oocytes include oocytes produced by meiosis in the ovaries. Oocytes include primary oocytes before the first meiosis and secondary oocytes in which the first meiosis has been completed.

In the present specification, the term "ovarian cavity fluid" means vaginal secretion near the ovaries in fish species in which the ovaries have been removed. Ovarian cavity fluid includes ovarian cavity fluid of fish in the ovulation phase.

The present invention will be specifically described below. Note that in the description below, "fish" means "marine fish" except when particularly noted.

1. Method of Maintaining Ovaries of Marine Fish

The method of maintaining ovaries of the present invention is a method including removing ovaries from marine fish, and culturing the removed ovaries or fragmented ovaries in a culture solution.

Here, removal means removing an organ (particularly the ovaries) from an individual, wherein the individuals from which organs are removed include live individuals. The removed organ may be an organ that is mixed, bound, joined, or adhered with another organ.

The ovaries that are the target of removal include those that have maintained function as an ovary, particularly those that contain oocytes.

The details of the culture solution used in the method of maintaining ovaries of the present invention will be described later herein.

The marine fish that are the target of ovarian removal may be harvested by any method provided that the fertilization capability of eggs contained in the ovaries is maintained. Fish harvested in the natural environment may be used, and artificially bred farmed fish may be used. Note that fish harvested in the natural environment include fish caught by fishing. This is because fish caught by fishing incur little damage and tend to maintain fertilization capability of eggs contained in the ovaries.

The fish used in removal of ovaries in the present invention are not particularly limited, but examples include yellowtail species exemplified by yellowtail and young yellowtail; amberjack species exemplified by greater amberjack and yellowtail amberjack; striped jack species; sea bream species exemplified by red sea bream, crimson sea bream, and silver sea bream; tuna species exemplified by Pacific bluefin tuna, Atlantic bluefin tuna, Southern bluefin tuna, yellow fin tuna, bigeye tuna, albacore tuna, longtail tuna, blackfin tuna, bonito, kawakawa, frigate mackerel, and bullet tuna; mackerel species exemplified by chub mackerel and blue mackerel; striped bonito species exemplified by striped bonito and dogtooth tuna; Spanish mackerel species exemplified by Japanese Spanish mackerel and wahoo; salmonid species exemplified by salmon and trout; flatfish species exemplified by flounder, plaice, and sole; and the like. These may be fish harvested in the natural environment or farmed fish.

The target of the method of maintaining ovaries of the present invention includes fish of the Scombridae family. A Scombridae family fish means a fish classified into the Scombrinae subfamily of the Scombridae family of the Perciformes order. Scombridae family fish include the Sardini tribe, Scomberomorini tribe, Scombrini tribe, and Thunnini tribe. The Sardini tribe includes the *Gymnosarda* genus and *Sarda* genus; the Scomberomorini tribe includes the *Acanthocybium* genus, *Grammatorcynus* genus, and *Scomberomorus* genus; the Scombrini tribe includes the *Rastrelliger* genus and *Scomber* genus; and the Thunnini tribe includes the *Auxis* genus, *Euthynnus* genus, *Katsuwonus* genus, and *Thunnus* genus. The *Gymnosarda* genus includes dogtooth tuna; the *Sarda* genus includes striped bonito; the *Acanthocybium* genus includes wahoo; the *Scomberomorus* genus includes Japanese Spanish mackerel; the *Scomber* genus includes chub mackerel and blue mackerel; the *Auxis* genus includes frigate mackerel and bullet tuna; the *Euthynnus* genus includes kawakawa; the *Katsuwonus* genus includes bonito; and the *Thunnus* genus includes Pacific bluefin tuna, Atlantic bluefin tuna, Southern bluefin tuna, yellowfin tuna, bigeye tuna, albacore tuna, longtail tuna, and blackfin tuna. Among Scombridae family fish, the *Thunnus* genus is one of the targets of the method of maintaining ovaries of the present invention.

The fish used in ovarian removal may be those that have reached the minimum number of years of maturation of that species and possess matured ovaries. This is because in fish that possess matured ovaries, the eggs contained in the ovaries often have fertilization capability.

Among fish possessing matured ovaries, the fish used in ovarian removal may be fish in the spawning period. This is because in fish in the spawning period, the eggs contained in the ovaries often have fertilization capability.

The fish used in ovarian removal may be fish possessing ovaries having transparent eggs. This is because in fish that possess transparent eggs, the eggs contained in the ovaries often have fertilization capability.

The fish from which ovaries are removed may be live fish, fish immediately after cardiac arrest, or cryopreserved fish as long as the eggs contained in the ovaries have fertilization capability.

Ovarian is removed as quickly as possible so that the eggs contained in the ovaries do not lose fertilization capability. This is because if removal takes time, the fertilization capability of the eggs contained in the ovaries ends up decreasing.

The term "maintaining ovaries" in the method of maintaining ovaries of the present invention means maintaining the eggs contained in the ovaries in a fertilizable state. Maintaining ovaries includes maintaining removed ovaries. Maintaining ovaries also includes maintaining a portion of removed ovaries, maintaining removed ovaries after cleaving, cutting, crushing, or decomposing them, and maintaining cleaved, cut, crushed, or decomposed ovaries in a state in which they have been mixed, bound, joined, or adhered with other cells, tissues, or organs.

In the present specification, the term "culturing" means holding for a certain period while maintaining the activity of cells, tissues, or organs. The term "culturing in a culture solution" means holding cells, tissues, or organs in a culture solution in order to maintain desired activity.

Culturing in the method of maintaining ovaries of the present invention includes holding removed ovaries or fragmented ovaries for a certain period in order to maintain the ovaries. The holding period may be of any length provided that it is a period for which desired activity is maintained. Culturing includes static culturing, shake culturing, rotary culturing, and agitation culturing within a range that desired activity is maintained.

In the method of maintaining ovaries of the present invention, culturing in a culture solution includes culturing removed ovaries or fragmented ovaries in a culture solution in order to maintain the removed ovaries.

In the method of maintaining ovaries of the present invention, culturing removed ovaries or fragmented ovaries in a culture solution includes holding removed ovaries or fragmented ovaries in a culture solution from before the start of culturing, holding in a culture solution after culturing, removing a culture solution during culturing, exchanging a culture solution during culturing, modifying a culture solution during culturing, and combinations thereof.

Culturing of the ovaries may be culturing the whole ovaries or fragmenting the ovaries and culturing a portion thereof as long as the eggs contained in the ovaries maintain fertilization capability.

When the ovaries are fragmented, they may be fragmented into sizes of 1 mm square, 2 mm square, 5 mm square, from 1 cm to 10 cm square, 5 cm square, 2 cm square, and 1 cm square. This is because when fragments smaller than 1 mm square are obtained, the possibility of eggs contained in the ovaries being destroyed increases and fertilization capability may decrease. This is also because when fragments larger than 10 cm square are obtained, a large amount of culture solution is required, and additionally, the fertilization capability of the eggs contained in the ovaries or fragmented ovaries may decrease because the culture solution is not distributed over the ovaries or fragmented ovaries.

Culturing of the ovaries or fragmented ovaries may also be performed using ovaries or fragmented ovaries that contain transparent eggs. This is because ovaries or fragmented ovaries that contain transparent eggs contain a large number of eggs having fertilization capability.

Culturing of the ovaries or fragmented ovaries may be performed using ovaries or fragmented ovaries that contain not less than 10, not less than 50, or not less than 100 transparent eggs, and not greater than 10000, not greater than 1000, or not greater than 200 transparent eggs. This is because ovaries or fragmented ovaries that contain not less than 10 transparent eggs contain a large number of eggs having fertilization capability. This is also because, with ovaries or fragmented ovaries containing not less than 1000) transparent eggs, the size of the ovaries or fragmented ovaries is excessively large and a large amount of culture solution is required, and additionally, the fertilization capability of the eggs contained in the ovaries or fragmented ovaries may decrease because the culture solution is not distributed over the ovaries or fragmented ovaries.

Culturing of ovaries or fragmented ovaries may be performed such that the ovaries or fragmented ovaries are entirely covered by the culture solution. By so doing, the culture solution is distributed over the ovaries or fragmented ovaries and a decrease in the fertilization capability of the eggs contained in the ovaries or fragmented ovaries can be averted.

Culturing of ovaries or fragmented ovaries may be performed at a temperature close to the spawning temperature of the fish that is the target of ovarian removal. This is because if it is performed close to the spawning temperature, the eggs contained in the ovaries or fragmented ovaries tend to maintain fertilization capability and tend to ovulate after culturing. In Pacific bluefin tuna, the spawning temperature is not lower than 24° C., not lower than 25° C., or not lower than 26° C., and is not higher than 28° C., not higher than 27'C, or not higher than 26° C.

Culturing of ovaries or fragmented ovaries is performed for a period for which the eggs contained in the ovaries or fragmented ovaries maintain fertilization capability.

For example, in the case of Pacific bluefin tuna, culturing of ovaries or fragmented ovaries may be performed for not less than 1 minute, not less than 10 minutes, or not less than 30 minutes after the start of culturing. This is because if the culturing period is too short, the effect of culturing is not sufficiently obtained. In Pacific bluefin tuna, culturing of ovaries or fragmented ovaries may be terminated within 24 hours, within 16 hours, within 8 hours, or within 5 hours after the start of culturing. This is because if the culturing period is too long, the eggs contained in the ovaries or fragmented ovaries tend not to maintain fertilization capability.

The method of maintaining ovaries of the present invention allows eggs contained in ovaries to maintain fertilization capability, and allows eggs having fertilization capability to be ovulated. Furthermore, by maintaining ovaries, it is possible to increase the chances of obtaining eggs having fertilization capability and to efficiently obtain eggs, and artificial insemination is easy.

The culture solution used in the method of maintaining ovaries of the present invention will be described below.

A "culture solution" is a solution used to maintain activity of cells, tissues, and organs. The culture solution in the method of maintaining ovaries of the present invention (referred to as "culture solution of the present invention" or simply "culture solution" hereinafter) means a solution used to maintain ovaries.

The composition of the culture solution is a composition of components that contribute to maintaining desired activity in culturing. The composition of the culture solution may be determined at any point during the culturing period. The composition of the culture solution may be satisfied at any point during the culturing period provided that desired activity is maintained in culturing. The composition of the culture solution may be satisfied continuously during the culturing period, intermittently during the culturing period, or for only a portion of the culturing period, within a range in which desired activity can be maintained during culturing.

The components contained in the culture solution of the present invention is not particularly limited provided that they are components for maintaining fertilization capability of eggs contained in ovaries in culturing. The components contained in the culture solution of the present invention include solutions containing at least one of: positively charged metal ions exemplified by sodium ions, potassium ions, calcium ions, and magnesium ions; negatively charged ions exemplified by chloride ions and sulfate ions; buffering agents; sugars; and antibiotics. The culture solution of the present invention includes commercially available solutions, prepared solutions, cryopreserved solutions, diluted solutions, and concentrated solutions.

The method of concentration measurement of components contained in the culture solution may be a known method by which the target component concentrations can be measured.

An example in the case of positively charged metal ions is atomic absorption method. In the cases of sodium ions and potassium ions and the like, measurement may be performed by the ion selective electrode method.

A sodium ion is sodium that has electrolytically dissociated in a solution. Sodium that has electrolytically dissociated in the solution includes electrolytically dissociated sodium atoms. Sodium ions in the present invention include sodium ions that have electrolytically dissociated in a culture solution. Sodium ions typically have a monovalent positive charge in the culture solution.

Sodium ions that have electrolytically dissociated in the culture solution are sodium ions that contribute to maintaining desired activity in culturing. Sodium ions that have electrolytically dissociated in the culture solution include sodium ions that have been chelated with a chelating agent to contribute to maintaining desired activity. Sodium ions that have electrolytically dissociated in the culture solution do not include sodium ions that have precipitated, crystallized, solidified, or complexed and that do not contribute to maintaining desired activity.

A potassium ion is potassium that has electrolytically dissociated in a solution. Potassium that has electrolytically dissociated in the solution includes electrolytically dissociated potassium atoms. Potassium ions include potassium ions that have electrolytically dissociated in a culture solution. Potassium ions typically have a monovalent positive charge in the culture solution.

Potassium ions that have electrolytically dissociated in the culture solution are potassium ions that contribute to maintaining desired activity in culturing. Potassium ions that have electrolytically dissociated in the culture solution include potassium ions that have been chelated with a chelating agent to contribute to maintaining desired activity. Potassium ions that have electrolytically dissociated in the culture solution do not include potassium ions that have precipitated, crystallized, solidified, or complexed and that do not contribute to maintaining desired activity.

A calcium ion is calcium that has electrolytically dissociated in a solution. Calcium that has electrolytically dissociated in the solution includes electrolytically dissociated calcium atoms. Calcium ions include calcium ions that have electrolytically dissociated in a culture solution. Calcium ions typically have a divalent positive charge in the culture solution.

Calcium ions that have electrolytically dissociated in the culture solution are calcium ions that contribute to maintaining desired activity in culturing. Calcium ions that have electrolytically dissociated in the culture solution include calcium ions that have been chelated with a chelating agent to contribute to maintaining desired activity. Calcium ions that have electrolytically dissociated in the culture solution do not include calcium ions that have precipitated, crystallized, solidified, or complexed and that do not contribute to maintaining desired activity.

A magnesium ion is magnesium that has electrolytically dissociated in a solution. Magnesium that has electrolytically dissociated in the solution includes electrolytically dissociated magnesium atoms. Magnesium ions include magnesium ions that have electrolytically dissociated in a culture solution. Magnesium ions typically have a divalent positive charge in the culture solution.

Magnesium ions that have electrolytically dissociated in the culture solution are magnesium ions that contribute to maintaining desired activity in culturing. Magnesium ions that have electrolytically dissociated in the culture solution include magnesium ions that have been chelated with a chelating agent to contribute to maintaining desired activity. Magnesium ions that have electrolytically dissociated in the culture solution do not include magnesium ions that have precipitated, crystallized, solidified, or complexed and that do not contribute to maintaining desired activity.

A chloride ion is chlorine that has electrolytically dissociated in a solution. Chlorine that has electrolytically dissociated in the solution includes electrolytically dissociated chlorine atoms. Chloride ions include chloride ions that have electrolytically dissociated in a culture solution. Chloride ions typically have a monovalent negative charge in the culture solution.

Chloride ions that have electrolytically dissociated in the culture solution are chloride ions that contribute to maintaining desired activity in culturing. Chloride ions that have electrolytically dissociated in the culture solution do not include chloride ions that have precipitated, crystallized, solidified, or complexed and that do not contribute to maintaining desired activity.

A sulfate ion is sulfuric acid that has electrolytically dissociated in a solution. In a solution, sulfuric acid that has electrolytically dissociated in the solution includes sulfate molecules consisting of one sulfur atom and four oxygen atoms. Sulfate ions include sulfate ions that have dissociated in a culture solution. Sulfate ions typically have a divalent negative charge in the culture solution.

Sulfate ions that have electrolytically dissociated in the culture solution are sulfate ions that contribute to maintaining desired activity in culturing. Sulfate ions that have electrolytically dissociated in the culture solution do not include sulfate ions that have precipitated, crystallized, solidified, or complexed and that do not contribute to maintaining desired activity.

The culture solution is adjusted by mixing individual components that will result in the predetermined composition. The pH of the culture solution used in culturing of ovaries or fragmented ovaries may be adjusted to within a range from +0.5 to −0.5, a range from +0.3 to −0.3, or a range from +0.1 to −0.1 relative to the pH of ovarian cavity fluid of the fish from which the ovaries have been removed. The reason that the pH of the culture solution used in culturing of ovaries or fragmented ovaries may be adjusted to within a range from +0.5 to −0.5, a range from +0.3 to −0.3, or a range from +0.1 to −0.1 relative to the pH of ovarian cavity fluid of the fish from which the ovaries have been removed is because the stress on the eggs contained in the ovaries or fragmented ovaries is small and the fertilization capability of the eggs contained in the ovaries or fragmented ovaries tends to be maintained. To adjust the pH of the culture solution, a Good's buffer exemplified by EPPS, MES, HEPES, PIPES, TES, ADA, BES, and ACES may be used. This is because when a Good's buffer is used, the stress on the eggs contained in the ovaries or fragmented ovaries is small and the fertilization capability of the eggs contained in the ovaries or fragmented ovaries tends to be maintained.

The positively charged metal ions contained in the culture solution are not limited, but examples include sodium ions, potassium ions, calcium ions, and magnesium ions. This is because, due to the presence of the above positively charged metal ions in the culture solution, osmotic pressure increases, and due to the physiological action of positively charged metal ions, the stress on the eggs contained in the ovaries or fragmented ovaries is reduced and the fertilization capability of the eggs contained in the ovaries or fragmented ovaries tends to be maintained and/or ovulation of the eggs contained in the cultured ovaries or fragmented ovaries is stimulated.

Positively charged metal ions exemplified by sodium ions, potassium ions, calcium ions, and magnesium ions may be included each alone or in combinations of two or more types. To maintain the fertilization capability of the eggs contained in the ovaries or fragmented ovaries, the above culture solution may contain not less than two, not less than three, or not less than four types among sodium ions, potassium ions, calcium ions, and magnesium ions. This is because the culture solution that contains many types of positively charged metal ions is well-balanced and a synergistic effect based on all the contained positively charged metal ions can be expected.

Sodium ions act on at least one of sodium ion channels and sodium-binding proteins, and contribute to maintaining fertilization capability of eggs contained in the ovaries or fragmented ovaries. The above sodium-binding proteins include those known as calcium-binding proteins exemplified by annexins.

Sodium ions are contained in the culture solution in a molar concentration of not less than 10 mM, not less than 50 mM, not less than 100 mM, not less than 120 mM, or not less than 150 mM, and in a molar concentration of not greater than 500 mM, not greater than 300 mM, not greater than 250 mM, not greater than 200 mM, or not greater than 150 mM. For example, they may be contained in a range of not less than 120 mM and not greater than 250 mM. This is because if there are too few sodium ions, the effect of adding sodium ions to the culture solution is small, and if there are too many sodium ions, the eggs contained in the ovaries or fragmented ovaries tend not to maintain fertilization capability.

Potassium ions act on at least one of potassium ion channels and potassium-binding proteins, and contribute to maintaining fertilization capability of eggs contained in the ovaries or fragmented ovaries. Potassium-binding proteins include proteins containing a carbohydrate chain recognition domain, exemplified by Emp46p and Emp47p.

Potassium ions are contained in the culture solution in a molar concentration of not less than 1.0 mM, not less than 2.0 mM, not less than 3.0 mM, not less than 5.0 mM, or not less than 7.0 mM, and in a molar concentration of not greater than 20 mM, not greater than 15 mM, not greater than 10 mM, not greater than 8.0 mM, or not greater than 7.0 mM. For example, potassium ions may be contained in a range of not less than 5 mM and not greater than 10 mM. This is because if there are too few potassium ions, the effect of adding potassium ions to the culture solution is small, and if there are too many potassium ions, the eggs contained in the ovaries or fragmented ovaries tend not to maintain fertilization capability.

Calcium ions act on at least one of calcium ion channels and calcium-binding proteins, and contribute to maintaining fertilization capability of eggs contained in the ovaries or fragmented ovaries. The above calcium-binding proteins are exemplified by catabolic enzymes including protease, phospholipase A2, and amylase, phopholipase b kinase, calcium transport ATPase, calsequestrin, calexcitin, and troponin.

Calcium ions are contained in the culture solution in a molar concentration of not less than 0.1 mM, not less than 0.5 mM, not less than 0.8 mM, not less than 1.0 mM, or not less than 1.5 mM, and in a molar concentration of not greater than 5.0 mM, not greater than 4.0 mM, not greater than 3.5 mM, not greater than 3.0 mM, or not greater than 2.0 mM. For example, calcium ions may be contained in a range of not less than 1.5 mM and not greater than 5.0 mM. This is because if there are too few calcium ions, the effect of adding calcium ions to the culture solution is small, and if there are too many calcium ions, the eggs contained in the ovaries or fragmented ovaries tend not to maintain fertilization capability.

Magnesium ions act on at least one of magnesium ion channels and magnesium-binding proteins, and contribute to maintaining fertilization capability of eggs contained in the ovaries or fragmented ovaries. The above magnesium-binding proteins include RNA-binding proteins exemplified by RNA polymerase, or magnesium transport proteins exemplified by paracellin.

Magnesium ions are contained in the culture solution in a molar concentration of not less than 0.1 mM, not less than 0.3 mM, not less than 0.5 mM, not less than 1.0 mM, or not less than 1.5 mM, and in a molar concentration of not greater than 5.0 mM, not greater than 3.0 mM, not greater than 2.0 mM, not greater than 1.8 mM, or not greater than 1.5 mM. For example, magnesium ions may be contained in a range of not less than 1.0 mM and not greater than 2.0 mM. This is because if there are too few magnesium ions, the effect of adding magnesium ions to the culture solution is small, and if there are too many magnesium ions, the eggs contained in the ovaries or fragmented ovaries tend not to maintain fertilization capability.

The composition of sodium ions, potassium ions, calcium ions, and magnesium ions in the culture solution used in culturing of ovaries or fragmented ovaries may be close to that of the sodium ions, potassium ions, calcium ions, and magnesium ions in blood serum of a fish in the spawning period, wherein the fish is the marine fish used in ovarian removal or a fish of the same species as the marine fish used in ovarian removal.

The molar concentrations of sodium ions, potassium ions, calcium ions, and magnesium ions in the culture solution may be molar concentrations from $1/4$ to 4 times, respective molar concentrations from $1/2$ to 2 times, or respectively molar concentrations from $2/3$ to 1.5 times the respective molar concentrations of sodium ions, potassium ions, calcium ions, and magnesium ions in blood serum of the marine fish used in ovarian removal. This is because when the molar concentrations of sodium ions, potassium ions, calcium ions, and magnesium ions in the culture solution are close to those of the sodium ions, potassium ions, calcium ions, and magnesium ions in blood serum of a fish in the spawning period, wherein the fish is the marine fish used in ovarian removal or a fish of the same species as the marine fish used in ovarian removal, the stress of removal can be mitigated, which contributes to maintaining the fertilization capability of eggs contained in the ovaries or fragmented ovaries.

When the fish in the spawning period that is the same species as the marine fish used in ovarian removal is a tuna, a fish having a body weight from 20 kg to 100 kg and particularly a fish from 40 kg to 80 kg may be selected. This is because when body weight is too low, properties as eggs may be insufficient even in the spawning period, and when body weight is too high, sampling exemplified by catching and obtaining blood serum tends to become difficult.

As the molar concentration ratio of sodium ions and potassium ions in the culture solution, when sodium ions are taken as 1, potassium ions may be set to not less than $1/100$, not less than $1/50$, or not less than $1/25$. At the same time, as the ratio of sodium ions and potassium ions in the culture solution, when sodium ions are taken as 1, potassium ions may be set to not greater than $1/20$, not greater than $1/10$, or not greater than $1/5$. When the ratio of sodium ions to potassium ions is too large, the hindrance effect of sodium ions is strong and the deficiency effect of potassium ions is relatively strong. Conversely, when the ratio of sodium ions to potassium ions is too small, the deficiency effect of sodium ions is strong and the hindrance effect of potassium ions is strong.

As the molar concentration ratio of sodium ions and calcium ions in the culture solution, when sodium ions are taken as 1, calcium ions may be set to not less than $1/200$, not less than $1/100$, or not less than $1/50$. At the same time, as the ratio of sodium ions and calcium ions in the culture solution, when sodium ions are taken as 1, calcium ions may be set to not greater than $1/40$, not greater than $1/20$, or not greater than $1/10$. When the ratio of sodium ions to calcium ions is too large, the hindrance effect of sodium ions is strong and the deficiency effect of calcium ions is relatively strong. Conversely, when the ratio of sodium ions to calcium ions is too small, the deficiency effect of sodium ions is strong and the hindrance effect of calcium ions is strong.

As the molar concentration ratio of sodium ions and magnesium ions in the culture solution, when sodium ions are taken as 1, magnesium ions may be set to not less than $1/1000$, not less than $1/500$, or not less than $1/250$. At the same time, as the ratio of sodium ions and magnesium ions in the culture solution, when sodium ions are taken as 1, magnesium ions may be set to not greater than $1/200$, not greater than $1/100$, or not greater than $1/50$. When the ratio of sodium ions to magnesium ions is too large, the hindrance effect of sodium ions is strong and the deficiency effect of magnesium ions is relatively strong. Conversely, when the ratio of sodium ions to magnesium ions is too small, the deficiency effect of sodium ions is strong and the hindrance effect of magnesium ions is strong.

As the molar concentration ratio of potassium ions and calcium ions in the culture solution, when potassium ions are taken as 1, calcium ions may be set to not less than $1/10$, not less than $1/5$, or not less than $1/3$. At the same time, as the ratio of potassium ions and calcium ions in the culture solution, when potassium ions are taken as 1, calcium ions may be set to not greater than $1/2$, not greater than 1, or not greater than 2. When the ratio of potassium ions to calcium ions is too large, the hindrance effect of potassium ions is strong and the deficiency effect of calcium ions is relatively strong. Conversely, when the ratio of potassium ions to calcium ions is too small, the deficiency effect of potassium ions is strong and the hindrance effect of calcium ions is strong.

As the molar concentration ratio of potassium ions and magnesium ions in the culture solution, when potassium ions are taken as 1, magnesium ions may be set to not less than 1/50, not less than 1/25, or not less than 1/10. At the same time, as the ratio of potassium ions and magnesium ions in the culture solution, when potassium ions are taken as 1, magnesium ions may be set to not greater than 1/8, not greater than 1/4, or not greater than 1/2. When the ratio of potassium ions to magnesium ions is too large, the hindrance effect of potassium ions is strong and the deficiency effect of magnesium ions is relatively strong. Conversely, when the ratio of potassium ions to magnesium ions is too small, the deficiency effect of potassium ions is strong and the hindrance effect of magnesium ions is strong.

As the molar concentration ratio of calcium ions and magnesium ions in the culture solution, when calcium ions are taken as 1, magnesium ions may be set to not less than 1/25, not less than 1/10, or not less than 1/5. At the same time, as the ratio of calcium ions and magnesium ions in the culture solution, when calcium ions are taken as 1, magnesium ions may be set to not greater than 1/4, not greater than 1/2, or not greater than 1. When the ratio of calcium ions to magnesium ions is too large, the hindrance effect of calcium ions is strong and the deficiency effect of magnesium ions is relatively strong. Conversely, when the ratio of calcium ions to magnesium ions is too small, the deficiency effect of calcium ions is strong and the hindrance effect of magnesium ions is strong.

The molar concentration ratios of sodium ions, potassium ions, and calcium ions in the culture solution may be set within any of the following ranges (1) to (3).
(1) When sodium ions are taken as 1, potassium ions are from 1/40 to 1/10, and calcium ions are from 1/100 to 1/25
(2) When potassium ions are taken as 1, sodium ions are from 10 to 40, and calcium ions are from 1/4 to 1
(3) When calcium ions are taken as 1, sodium ions are from 25 to 100, and potassium ions are from 1 to 4

The appropriate molar concentration of each type of ion reflects the state of activity in vivo, and can achieve the desired effect in a low stress state.

The molar concentration ratios of sodium ions, potassium ions, and magnesium ions in the culture solution may be set within any of the following ranges (1) to (3).
(1) When sodium ions are taken as 1, potassium ions are from 1/40 to 1/10, and magnesium ions are from 1/400 to 1/100
(2) When potassium ions are taken as 1, sodium ions are from 10 to 40, and magnesium ions are from 1/16 to 1/4
(3) When magnesium ions are taken as 1, sodium ions are from 100 to 400, and potassium ions are from 4 to 16

The appropriate molar concentration of each type of ion reflects the state of activity in vivo, and can achieve the desired effect in a low stress state.

The molar concentration ratios of sodium ions, calcium ions, and magnesium ions in the culture solution may be set within any of the following ranges (1) to (3).
(1) When sodium ions are taken as 1, calcium ions are from 1/100 to 1/25, and magnesium ions are from 1/400 to 1/100
(2) When calcium ions are taken as 1, sodium ions are from 25 to 100, and magnesium ions are from 1/8 to 1/2
(3) When magnesium ions are taken as 1, sodium ions are from 100 to 400, and calcium ions are from 2 to 8

The appropriate molar concentration of each type of ion reflects the state of activity in vivo, and can achieve the desired effect in a low stress state.

The molar concentration ratios of potassium ions, calcium ions, and magnesium ions in the culture solution may be set within any of the following ranges (1) to (3).
(1) When potassium ions are taken as 1, calcium ions are from 1/4 to 1, and magnesium ions are from 1/16 to 1/4
(2) When calcium ions are taken as 1, potassium ions are from 1 to 4, and magnesium ions are from 1/8 to 1/2
(3) When magnesium ions are taken as 1, potassium ions are from 4 to 16, and calcium ions are from 2 to 8

The appropriate molar concentration of each type of ion reflects the state of activity in vivo, and can achieve the desired effect in a low stress state.

The molar concentration ratios of sodium ions, potassium ions, calcium ions, and magnesium ions in the culture solution may be set within any of the following ranges (1) to (3).
(1) When sodium ions are taken as 1, potassium ions are from 1/40 to 1/10, calcium ions are from 1/100 to 1/25, and magnesium ions are from 1/400 to 1/100
(2) When potassium ions are taken as 1, sodium ions are from 10 to 40, calcium ions are from 1/4 to 1, and magnesium ions are from 1/16 to 1/4
(3) When calcium ions are taken as 1, sodium ions are from 25 to 100, potassium ions are from 1 to 4, and magnesium ions are from 1/8 to 1/2
(4) When magnesium ions are taken as 1, sodium ions are from 100 to 400, potassium ions are from 4 to 16, and calcium ions are from 2 to 8

The appropriate molar concentration of each type of ion reflects the state of activity in the body, and can achieve the desired effect in a low stress state.

The negatively charged ions contained in the culture solution are not limited, but examples include chloride ions and sulfate ions. This is because, due to the presence of the above negatively charged ions in the culture solution, osmotic pressure increases, and due to the physiological action of negatively charged ions, the stress on the eggs contained in the ovaries or fragmented ovaries is reduced and the fertilization capability of the eggs contained in the ovaries or fragmented ovaries tends to be maintained and/or ovulation of the eggs contained in the cultured ovaries or fragmented ovaries is stimulated.

The above negatively charged ions exemplified by chloride ions and sulfate ions may be included each alone or in combinations of two or more types. To maintain the fertilization capability of the eggs contained in the ovaries or fragmented ovaries, the above culture solution may contain both chloride ions and sulfate ions. This is because the culture solution that contains many types is well-balanced and a synergistic effect based on all of the contained negatively charged ions can be expected.

Chloride ions act on at least one of chloride ion channels and chloride ion-binding proteins, and contribute to maintaining fertilization capability of eggs contained in the ovaries or fragmented ovaries. The above chloride ion-binding proteins include those known as chloride ion-binding proteins exemplified by chloride ion channels.

Chloride ions are contained in the culture solution at a concentration of not less than 50 mM, 100 mM, 150 mM, or 200 mM, and not greater than 500 mM, 300 mM, 250 mM, or 200 mM. For example, chloride ions may be contained in a range of not less than 150 mM and not greater than 250 mM. This is because if there are too few chloride ions, the effect of adding chloride ions to the culture solution is small, and if there are too many chloride ions, the eggs contained in the ovaries or fragmented ovaries tend not to maintain fertilization capability.

Sulfate ions act on at least one of sulfate ion channels and sulfate ion-binding proteins, and contribute to maintaining fertilization capability of eggs contained in the ovaries or fragmented ovaries. Sulfate ion-binding proteins include proteins that bind to sulfate ions exemplified by sulfate ion transporters.

Sulfate ions are contained in the culture solution at a concentration of not less than 1 mM, 10 mM, 50 mM, 100 mM, or 200 mM, and not greater than 500 mM, 300 mM, 250 mM, or 200 mM. For example, sulfate ions may be contained in a range of not less than 100 mM and not greater than 250 mM. This is because if there are too few sulfate ions, the effect of adding sulfate ions to the culture solution is small, and if there are too many sulfate ions, the eggs contained in the ovaries or fragmented ovaries tend not to maintain fertilization capability.

As the molar concentration ratio of chloride ions and sulfate ions in the culture solution used in culturing ovaries or fragmented ovaries, when chloride ions are taken as 1, sulfate ions may be set to not less than 10, not less than 25, or not less than 50. At the same time, as the ratio of chloride ions and sulfate ions in the culture solution used in culturing ovaries or fragmented ovaries, when chloride ions are taken as 1, sulfate ions may be set to not greater than 400, not greater than 200, or not greater than 100. When the ratio of chloride ions to sulfate ions is too large, the hindrance effect of chloride ions is strong and the deficiency effect of sulfate ions is relatively strong. When the ratio of chloride ions to sulfate ions is too small, the deficiency effect of chloride ions is strong and the hindrance effect of sulfate ions is strong.

As the molar concentration ratio of positively charged metal ions and negatively charged ions in the culture solution, when positively charged metal ions are taken as 1, negatively charged ions may be set to not less than 0.5, not less than 0.7, or not less than 0.9. At the same time, as the ratio of positively charged metal ions and negatively charged ions in the culture solution, when positively charged metal ions are taken as 1, negatively charged ions may be set to not greater than 1.5, not greater than 1.3, or not greater than 1.1. When the ratio of positively charged metal ions to negatively charged ions is too large, the hindrance effect of positively charged metal ions is strong and the deficiency effect of negatively charged ions is relatively strong. When the ratio of positively charged metal ions to negatively charged ions is too small, the deficiency effect of positively charged metal ions is strong and the hindrance effect of negatively charged ions is strong.

The culture solution may contain sugars. This is because, due to the presence of the above sugars in the culture solution, osmotic pressure increases, and due to the fact that it acts as an energy source or acts as a signal molecule, the stress on the eggs contained in the ovaries or fragmented ovaries is reduced and the fertilization capability of the eggs contained in the ovaries or fragmented ovaries tends to be maintained and/or ovulation of the eggs contained in the cultured ovaries or fragmented ovaries is stimulated.

The type of sugar contained in the culture solution is not particularly limited provided that the object of the present invention is not lost, but examples include glucose, galactose, fructose, and sucrose. This is because the utilization efficiency of glucose, galactose, fructose, and sucrose as energy in cells is high and the fertilization capability of the eggs contained in the ovaries or fragmented ovaries is easily maintained, and/or a large effect of stimulating ovulation of eggs contained in the cultured ovaries or fragmented ovaries can be expected. One type of sugar alone may be included or combinations of two or more types may be included.

The above sugars are contained in the culture solution in a molar concentration of not less than 0.1 mM, not less than 1.0 mM, not less than 3.0 mM, or not less than 5.0 mM, and in a molar concentration of not greater than 100 mM, not greater than 50 mM, not greater than 20 mM, not greater than 10 mM, or not greater than 5.0 mM. This is because if there is too little sugar, the effect of adding sugar to the culture solution is small, and if there is too much sugar, the eggs contained in the ovaries or fragmented ovaries tend not to maintain fertilization capability.

The culture solution may contain antibiotics. This is because, the presence of antibiotics in the culture solution weakens bacterial proliferation and thereby the eggs contained in the ovaries or fragmented ovaries tend to maintain fertilization capability.

The type of antibiotic contained in the culture solution is not particularly limited provided that the object of the present invention is not lost. Examples thereof include penicillin antibiotics exemplified by benzylpenicillin potassium and ampicillin, and aminoglycoside antibiotics exemplified by kanamycin, streptomycin, gentamicin, and neomycin. The above antibiotics may be included each alone or in combinations of two or more types within a range in which an effect as an antibiotic is obtained and side effects do not occur. This is because penicillin and aminoglycoside antibiotics tend to provide effects as antibiotics in aquatic production systems.

The above antibiotics are included in the culture solution in a volume suitable for each antibiotic. When benzylpenicillin potassium is used as the above penicillin antibiotic, it is used in a concentration of not less than 10 mg/L, not less than 30 mg/L, not less than 50 mg/L, or not less than 70 mg/L, and not greater than 500 mg/L, not greater than 300 mg/L, not greater than 150 mg/L, or not greater than 70 mg/L. This is because when there is too little benzylpenicillin potassium, the effect of adding benzylpenicillin potassium is difficult to obtain, and when there is too much benzylpenicillin potassium, the eggs contained in the ovaries or fragmented ovaries tend not to maintain fertilization capability due to side effects.

When kanamycin sulfate is used as the above aminoglycoside antibiotic, it is used in a concentration of not less than 10 mg/L, not less than 20 mg/L, not less than 30 mg/L, or not less than 50 mg/L, and not greater than 500 mg/L, not greater than 300 mg/L, not greater than 100 mg/L, or not greater than 50 mg/L. This is because when there is too little kanamycin, the effect of adding kanamycin is difficult to obtain, and when there is too much kanamycin, the eggs contained in the ovaries or fragmented ovaries tend not to maintain fertilization capability due to side effects.

When streptomycin sulfate is used as the above aminoglycoside antibiotic, it is used in a concentration of not less than 10 mg/L, not less than 30 mg/L, not less than 60 mg/L, or not less than 100 mg/L, and not greater than 500 mg/L, not greater than 300 mg/L, not greater than 150 mg/L, or not greater than 100 mg/L. This is because when there is too little streptomycin, the effect of adding streptomycin is difficult to obtain, and when there is too much streptomycin, the eggs contained in the ovaries or fragmented ovaries tend not to maintain fertilization capability due to side effects.

The osmotic pressure of the culture solution may be not less than 100 mOsm/kg, not less than 200 mOsm/kg, or not less than 350 mOsm/kg, and not greater than 6000 mOsm/kg, not greater than 5000 mOsm/kg, or not greater than 4500 mOsm/kg. When the osmotic pressure is too low, the cells may receive low osmotic pressure stress, and fertilization capability of the eggs contained in the ovaries or fragmented ovaries may decrease. When the osmotic pressure is too high, the cells may receive high osmotic pressure stress, and fertilization capability of the eggs contained in the ovaries or fragmented ovaries may decrease.

The components that bear osmotic pressure in the culture solution are positively charged metal ions, negatively charged ions, and sugars, which may constitute not less than 90%, not less than 95%, or not less than 99% of the total osmotic pressure. Among glucose, galactose, fructose, and sucrose, one type or a combination of two or more types of sugar may be used.

Positively charged metal ions, negatively charged ions, and sugars may be used to adjust osmotic pressure in intracellular fluid and extracellular fluid in vivo, and the stress on cells is small.

As a component that bears osmotic pressure in the culture solution, positively charged metal ions may constitute not less than 1/3, not less than 2/5, or not less than 3/7, and not greater than 2/3, not greater than 3/5, or not greater than 4/7 of the total osmotic pressure.

As a component that bears osmotic pressure in the culture solution, negatively charged ions may constitute not less than 1/3, not less than 2/5, or not less than 3/7, and not greater than 2/3, not greater than 3/5, or not greater than 4/7 of the total osmotic pressure. When there are too many positively charged metal ions, there are relatively few negatively charged ions, and when there are too few positively charged metal ions, there are relatively many negatively charged ions. In either case, excessive stress may be imparted on the cells.

As a component that bears osmotic pressure in the culture solution, sugars may constitute not less than 1/3, not less than 2/5, or not less than 3/7, and not greater than 2/3, not greater than 3/5, or not greater than 4/7 of the total osmotic pressure.

When there is too little sugar, the cells receive metabolic stress, and when there is too much sugar, problems with the flowability of the culture solution may occur.

2. Method of Producing Eggs of Marine Fish

The method of producing eggs of marine fish of the present invention includes obtaining eggs by causing the ovaries cultured by the method of maintaining ovaries of the present invention to ovulate.

In the method of producing eggs of the present invention, ovulation is typically performed automatically by culturing the ovaries or fragmented ovaries in the culture solution. Ovulation can also be stimulated by any method or can be forcibly induced after removing the ovaries or fragmented ovaries from the culture solution, as long as the obtained eggs are not damaged.

The term "ovulation" means that follicles are split in the ovaries and eggs are discharged. Discharge of eggs includes eggs being discharged within the individual, as well as eggs being discharged to outside the ovaries in the case of ovaries that have been removed.

The "number of ovulated eggs" may be determined by counting the eggs separated from fragmented ovaries using a stereoscopic microscope and taking this number as the number of ovulated eggs, or by fixing the ovaries or fragmented ovaries with a fixing solution after culturing and counting the follicles after ovulation in the ovaries or fragmented ovaries. The "number of unovulated transparent eggs" may be determined by fixing the ovaries or fragmented ovaries with a fixing solution after culturing and counting the unovulated transparent eggs remaining in the ovaries or fragmented ovaries. The "ovulation rate" may be determined by dividing the number of ovulated eggs by the sum of the number of ovulated eggs and the number of remaining unovulated transparent eggs.

The method of producing fertilized eggs of the present invention includes obtaining fertilized eggs by cross-fertilizing eggs obtained by the method of producing eggs of the present invention and sperm. The eggs obtained by the above method of producing eggs of the present invention can be fertilized because they have fertilization capability, such that artificial insemination can be carried out systematically.

The term "sperm" means a male gamete produced in the testis. The sperm in the method of producing fertilized eggs of the present invention needs to have a fertilizing capacity, and include sperm spawned in the natural environment, sperm spawned by inducement in an artificial environment, sperm collected after removal of testis from a live individual, and cryopreserved sperm.

The term "cross-fertilizing eggs and sperm" means stimulating fertilization in an environment in which eggs and sperm are brought in contact. In the method of producing fertilized eggs of the present invention, cross-fertilization of the present invention includes that carried out in the natural environment or that carried out in an artificially prepared solution.

In the method of producing fertilized eggs of the present invention, cross-fertilization of eggs and sperm of the present invention may be carried out in the natural environment or may be carried out in an artificially prepared solution. Cross-fertilization of eggs and sperm may be performed with one egg and one or a plurality of sperm, or with a plurality of eggs and one or a plurality of sperm.

The term "fertilization" means that a sperm and an egg are joined and the sperm penetrates the egg. Fertilization in the method of producing fertilized eggs of the present invention includes that carried out in the natural environment or that carried out in an artificially prepared solution. In fertilization, sperm may be applied after the culture solution has been removed from the eggs.

The term "fertilized egg" means an egg that has been fertilized. The fertilized eggs in the method of producing fertilized eggs of the present invention include those that begin cell division after the sperm and egg are joined, those that float after cell division to become floating eggs, and those that are made transparent after floating to become transparent eggs.

The term "egg having fertilization capability" means an egg having the ability to be fertilized when the egg and sperm are cross-fertilized. In the method of producing fertilized eggs of the present invention, it is determined whether or not an egg is an egg having fertilization capability by whether or not the egg is fertilized after being contacted with sperm in an environment that does not hinder fertilization in that species.

3. Method of Rearing Marine Fish of the Present Invention, and Method of Producing Farmed Marine Fish of the Present Invention The method of rearing marine fish of the present invention includes rearing larvae hatched from fertilized eggs obtained by the above method of producing fertilized eggs of the present invention to young fry, immature fish, or adult fish. Furthermore, the method of producing farmed marine fish of the present invention includes rearing larvae hatched from fertilized eggs obtained by the above method of producing fertilized eggs of the present invention to young fry, immature fish, or adult fish.

That is, the fertilized eggs obtained by the method of producing fertilized eggs of the present invention may be hatched and used as hatched larvae, and then grown into immature fish and adult fish. Furthermore, due to the fact that fertilized eggs are systematically obtained, hatched larvae can also be obtained systematically, and seed production and aquaculture may be performed systematically and efficiently.

The term "larvae" means fish at a stage after being hatched from eggs until becoming young fry. Larvae include larvae hatched in the natural environment and in artificial environments.

The term "young fry" means the stage in which the larva grows until it becomes an immature fish. Young fry include fish that have reached a stage in which the number of fin rays or number of vertebrae has reached a certain number and the fish exhibits the features of the species.

The term "immature fish" means the stage in which the young fry grows until it becomes an adult fish. Immature fish include fish from the time when scales are formed until the fish reaches maturity.

The term "adult fish" means an immature fish that has grown and matured. Adult fish include fish that have reproductive capability after maturation and fish that have lost their reproductive capability after once having reproductive capability.

Fertilized eggs may be allowed to hatch by holding them for a certain time in seawater or an appropriate solution. The method is determined as appropriate in accordance with the species of target marine fish.

Immature fish and adult fish may be obtained from hatched larvae by breeding hatched larvae for a certain time in seawater or an appropriate environment. The breeding conditions are determined as appropriate in accordance with the species of target marine fish.

The larvae, young fry, immature fish, and adult fish obtained by the method of rearing marine fish (method of producing farmed marine fish) of the present invention may be sold as seed or as food.

In the present specification, the features of each invention described in embodiments related to each aspect of the invention may be combined as desired to form new embodiments, and it is to be understood that such new embodiments may be included in each of the aspects of the present invention.

EXAMPLES

The present invention is described specifically below by citing examples, but the present invention is not limited to these examples.

Example 1

Materials and Methods
(1) Tested Fish
Farmed Pacific bluefin tuna (average fish body weight: 86.4 kg) were used in this experiment. These fish were caught by round haul nets in the Sea of Japan and developed for three years. During the aquaculture period, the fish were fed frozen sand lance, sardine, horse mackerel, and mackerel.
(2) Collecting of Sperm
As the sperm used in the experiment, sperm released from the genital pore or sperm in removed testis of males that were caught for shipping were collected, and used as a mixture from one to three fish. Only sperm collected on the same day were used in the experiment.
(3) Culture Solution
The culture solution used had a composition containing 124.1 mM of sodium chloride, 5.1 mM of potassium chloride, 1.0 mM of magnesium sulfate, 1.6 mM of calcium chloride, and 5.6 mM of glucose. The culture solution was produced by mixing commercially available reagents manufactured by Wako Pure Chemical Industries, Ltd. The culture solution was used after adding 100) mg/L of streptomycin sulfate, 50 mg/L of kanamycin sulfate, and 70 mg/L of benzylpenicillin potassium as antibiotics. All antibiotics used were reagents manufactured by Wako Pure Chemical Industries, Ltd. Furthermore, since the Pacific bluefin tuna ovarian cavity fluid had an average pH of 8.0 (n=5, maximum pH 8.1, minimum pH 7.9), the culture solution was set to pH 8.0, and 10 mM of EPPS manufactured by Dojindo Laboratories was used as a buffer.

Example 2

Examination of Culture Solution

It was examined whether the culture solution used could maintain fertilization capability of eggs ovulated from Pacific bluefin tuna. In the experiment, eggs previously ovulated in vivo were used, and were collected from ovaries removed from one female fish that was caught by fishing for shipping. After collection of eggs, approximately 100 eggs each were distributed in a 12-well culture microplate manufactured by AGC Techno Glass Co., Ltd. The harvested eggs were divided into an untreated control section and a culture solution section which was washed with culture solution and then immersed in 2 mL of culture solution. Additionally, among the test groups, sections that were artificially inseminated at 0, 0.5, 1.0, 2.0, 4.0, 6.0, or 8.0 hours after the start of the experiment were set up. Note that 0 hours after the start of the experiment means immediately after the start.

The test sections were set up and the experiment was started quickly after collection of eggs, and the temperature was controlled to 26° C. and humidity to 100% until artificial insemination was performed. When artificial insemination was performed, after sperm were sufficiently distributed over the eggs, and seawater was added to cause fertilization. In the culture solution section, sperm were added after the culture solution was removed to the extent possible.

After artificial insemination, the flotation rate (100×number of floating eggs/total number of ovulated eggs used in experiment) and fertilization rate (flotation rate×number of fertilized eggs/number of floating eggs) were calculated by observation with a stereoscopic microscope SZ61 manufactured by Olympus Corporation. Additionally, approximately 20 eggs were randomly selected from the floating eggs and transferred to a 6-well culture microplate filled with 10 mL of seawater. They were managed until hatching, and the hatching rate (flotation rate×number of hatched larvae/number of transferred floating eggs) was determined. During management, dead eggs were removed as appropriate and water quality was maintained.

Figure 2:
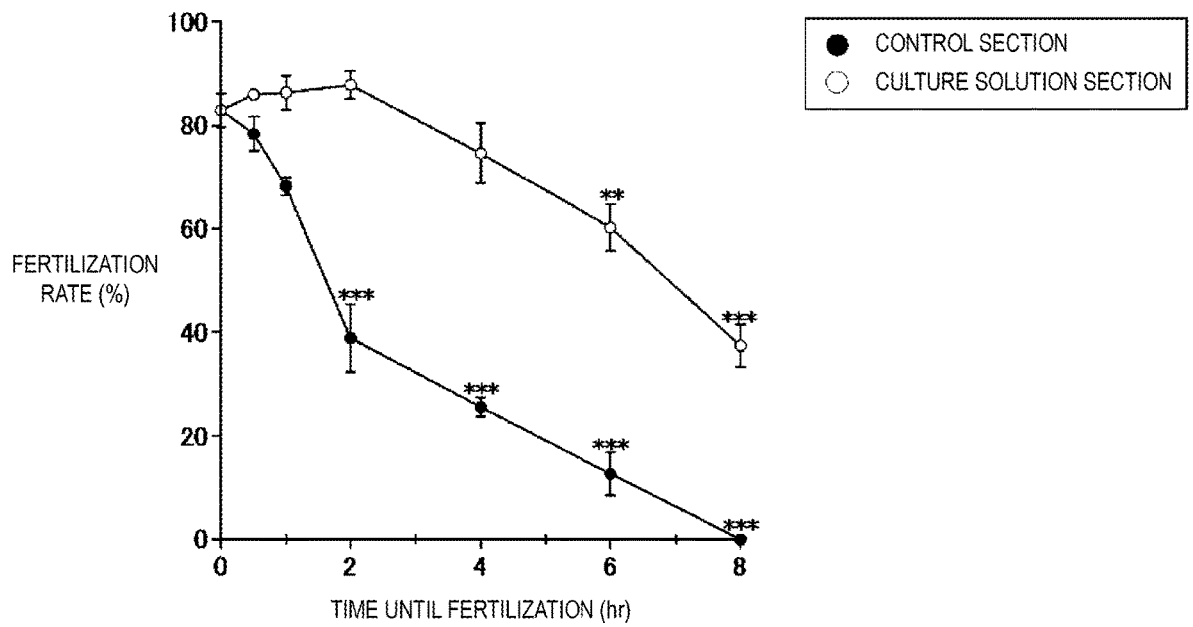
FIG. 2 is a graph showing fertilization rate versus fertilization time in the control section in which eggs ovulated in vivo are untreated and in the culture solution section in which eggs are immersed in culture solution. In the graph, the asterisks indicate a significant difference relative to 0 hours, wherein * means $P<0.05$,  means $P<0.01$, and * means $P<0.001$.
Figure 3:
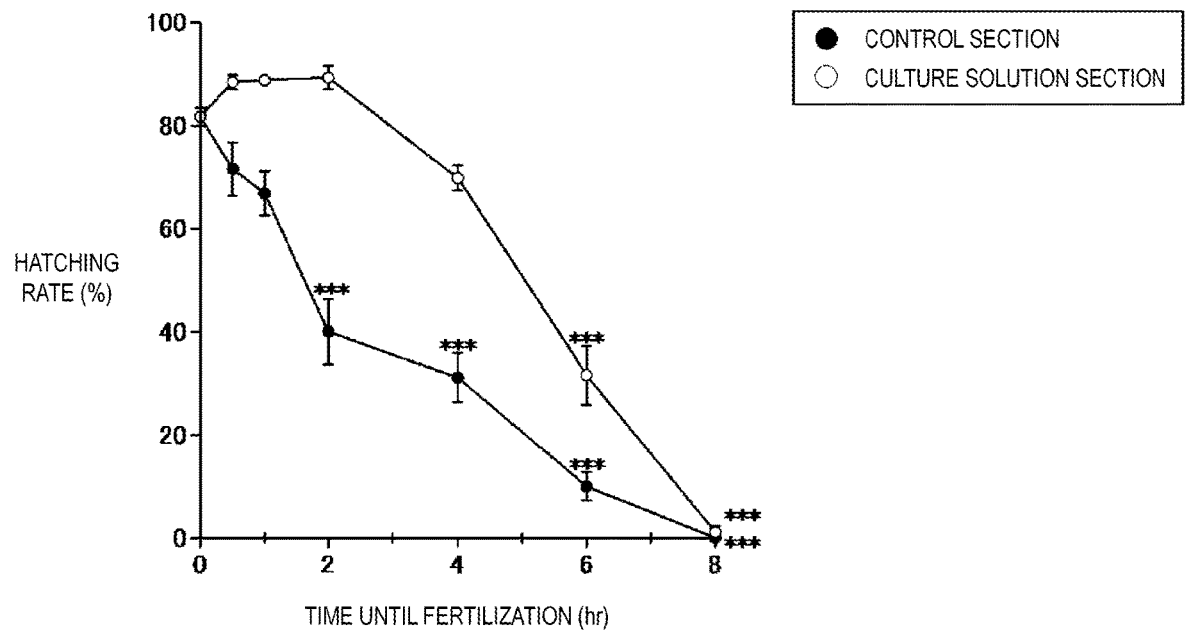
FIG. 3 is a graph showing hatching rate versus fertilization time in the control section in which eggs ovulated in vivo are untreated and in the culture solution section in which eggs are immersed in culture solution. In the graph, the asterisks indicate a significant difference relative to 0 hours, wherein * means $P<0.05$,  means $P<0.01$, and * means $P<0.001$.

As shown in FIGS. 1 to 3, the flotation rate, fertilization rate, and hatching rate of the control section were significantly lower than those of the section artificially inseminated after not less than 2 hours had elapsed. The flotation rate of the culture solution section was maintained up to 8 hours, and the fertilization rate and hatching rate exhibited a decreasing trend after 4 hours, and decreased significantly in sections after 6 or more hours. Thus, it was ascertained that ovulated eggs can maintain fertilization capability for up to 4 hours in the culture solution, and the culture solution can be used in the following culturing experiments.

Example 3

Examination of Ovary Treatment Method for Causing Ovulation Ex Vivo

A method for treating ovaries suitable for obtaining eggs in order to cause ovulation ex vivo was studied. Ovaries containing transparent eggs, which are oocytes that have become transparent, were used in the experiments. Ovaries removed from one female fish that was caught by fishing for shipping were used.

The removed ovaries were fragmented into approximately 1 cm squares in the culture solution, and these fragmented ovaries were distributed in 12-well culture microplates filled with 2 mL of culture solution so as to contain approximately 100 transparent eggs each. Taking 0 hours to be the point immediately after ovarian removal, experimental sections in which the above fragmentation and microplate distribution treatment was performed 0, 1, 2, and 3 hours later were set up, and a control section in which ovaries were held as is under the same conditions as the experimental group without undergoing the fragmentation and microplate distribution treatment was set up. In the experimental sections, sampling was performed every 0.5 hours up to 2 hours after the above fragmentation and microplate distribution treatment, and in the control section, sampling was performed every 0.5 hours up to 5 hours, taking 0 hours to be the point immediately after ovarian removal. During the experiment, the temperature was controlled to 26° C.

The ovulation rate was calculated from the sampled specimens. To calculate the ovulation rate, in the experimental sections, the eggs peeled off from fragmented ovaries in the wells of the culture plate were counted using a stereoscopic microscope, and in the control section, the number of follicles after ovulation in the sample ovaries fixed with 10% formalin (manufactured by Wako Pure Chemical Industries, Ltd.) were counted.

Furthermore, in all sections, the unovulated transparent eggs remaining in the 10% formalin-fixed fragmented ovaries or sample ovaries were counted. In the experimental sections, the ovulation rate was calculated by dividing the number of ovulated eggs by the sum of the number of ovulated eggs and the number of remaining unovulated transparent eggs. In the control section, it was calculated by dividing the number of ovulated eggs by the sum of the number of follicles after ovulation and the number of remaining unovulated transparent eggs. Additionally, the morphology of ovulated eggs 2 hours after fragmentation and microplate distribution treatment in each experimental section was observed using a stereoscopic microscope. As for the morphology of the eggs, the morphology of eggs ovulated in vivo obtained for each individual was determined to be a normal morphology, and eggs that were not spherical or that exhibited non-uniform brown components inside the egg were considered to have abnormal morphology.

Figure 4:
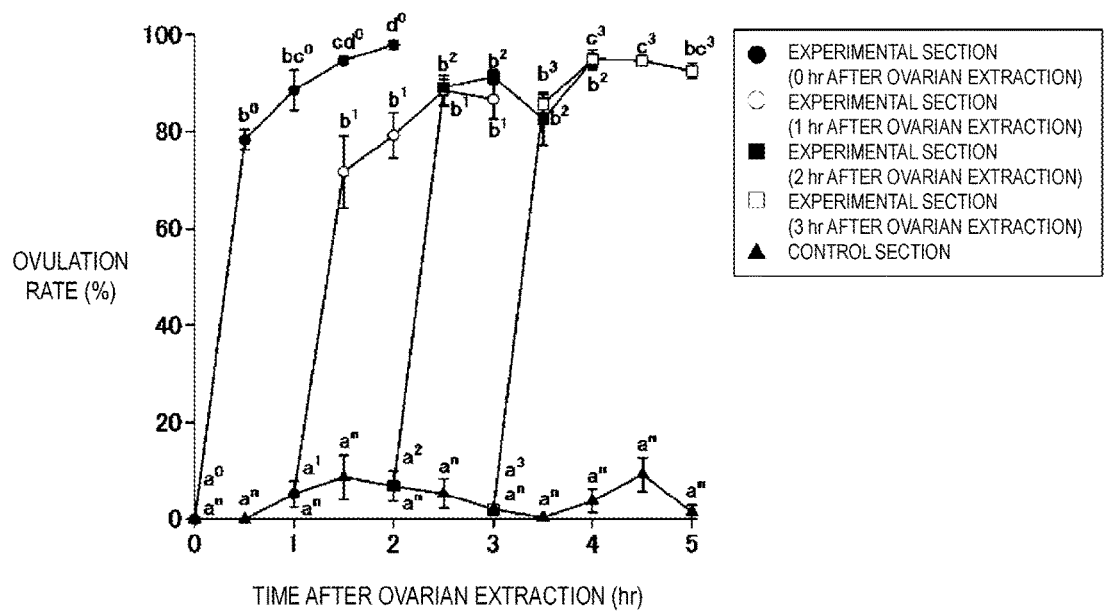
FIG. 4 is a graph showing the change in ovulation rate over time in the experimental sections at 0, 1, 2, or 3 hours after ovary removal and the control section. The different letters in the graph indicate the significant difference within the same experimental group, and the characters above the letters indicate the group.
Figure 5A:
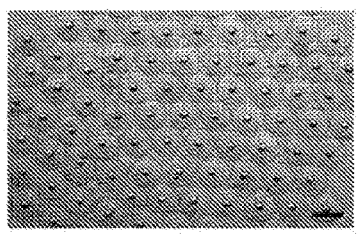
FIG. 5A shows the experimental section that underwent fragmentation and microplate distribution treatment 0 hours after ovarian removal.
Figure 5B:
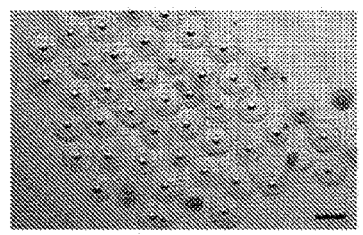
FIG. 5B shows the experimental section that underwent fragmentation and microplate distribution treatment 1 hour after ovarian removal.
Figure 5C:
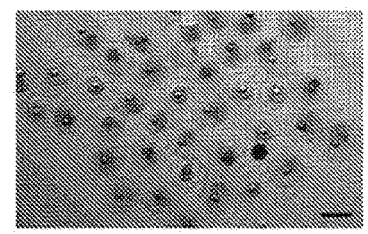
FIG. 5C shows the experimental section that underwent fragmentation and microplate distribution treatment 2 hours after ovarian removal.
Figure 5D:
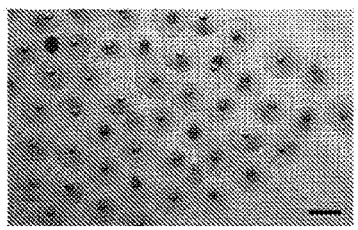
FIG. 5D shows the experimental section that underwent fragmentation and microplate distribution treatment 3 hours after ovarian removal.
Figure 5E:
FIG. 5E shows the control section.
Figure 5F:
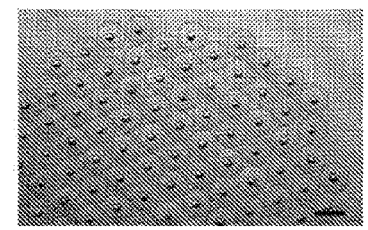
FIG. 5F shows the form of eggs ovulated in vivo obtained from another individual.

As shown in FIG. 4, in the experimental sections that underwent fragmentation and microplate distribution treatment 0, 1, 2, and 3 hours after ovarian removal, the ovulation rate rose significantly starting at 0.5 hours after fragmentation and microplate distribution treatment. However, no change in ovulation rate was seen in the control section.

Figure 6:
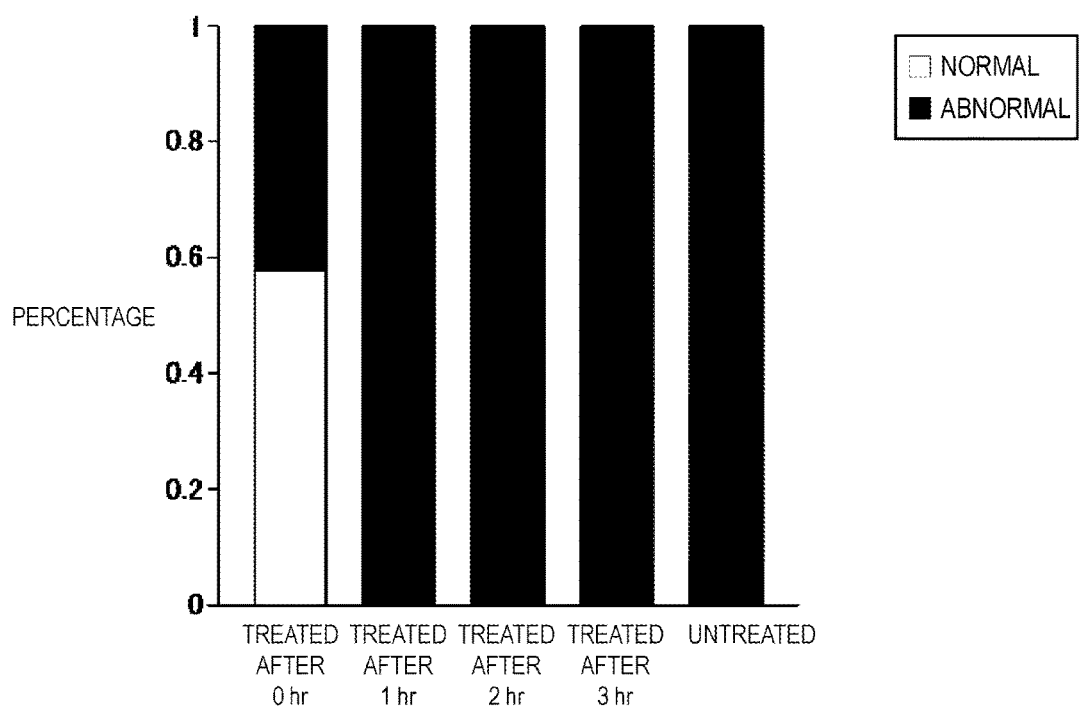
FIG. 6 is a graph showing the frequency of appearance of ovulated eggs exhibiting a normal or abnormal form in the experimental sections and the control section.

FIG. 5 shows the results of observation of ovulated eggs 2 hours after fragmentation and microplate distribution treatment in each experimental section. From the results of observation of ovulated eggs, the presence of eggs having a normal morphology as seen in in vivo ovulation was ascertained only in sections that underwent fragmentation and microplate distribution treatment immediately after ovarian removal. FIG. 6 shows the frequency of appearance of ovulated eggs exhibiting a normal or abnormal morphology in the experimental sections and the control section.

Thus, it was ascertained that ovulation occurs due to fragmentation treatment of ovaries, but fragmentation and microplate distribution treatment immediately after ovarian removal is necessary in order to obtain ex vivo ovulated eggs with a normal morphology thought to have fertilization capability.

Example 4

Ascertaining Fertilization Capability

Using ovaries of a total of seven fish, eggs cultured for 1 hour in culture solution and ovulated ex vivo were artificially inseminated, taking those that underwent fragmentation and microplate distribution treatment immediately after ovarian removal as 0 hours. FIG. 7 shows photographs of fertilized eggs and hatched larvae obtained from ovulation ex vivo. Furthermore, Table 1 shows the ovulation rate, flotation rate, fertilization rate, and hatching rate in each individual.

As a result, larvae were obtained from five fish, although individual differences in egg quality were observed.

TABLE 1

| Individual no. | Ovulation rate (%) | Flotation rate (%) | Fertilization rate (%) | Hatching rate (%) |
| --- | --- | --- | --- | --- |
| 1 | 97.7 ± 0.4 | 93.7 ± 1.4 | 23.6 ± 7.2 | 18.3 ± 6.7 |
| 2 | 98.0 ± 2.0 | 96.6 ± 0.9 | 75.4 ± 1.2 | 58.9 ± 0.5 |
| 3 | 53.5 ± 6.8 | 83.0 ± 3.0 | 0.0 ± 0.0 | 0.0 ± 0.0 |
| 4 | 98.1 ± 1.4 | 95.7 ± 0.5 | 50.8 ± 7.4 | 40.8 ± 7.7 |
| 5 | 94.5 ± 1.5 | 91.6 ± 1.5 | 46.0 ± 6.6 | 29.0 ± 3.5 |
| 6 | 98.4 ± 0.8 | 96.9 ± 1.0 | 51.2 ± 5.0 | 46.0 ± 9.9 |
| 7 | 67.7 ± 14.7 | 78.6 ± 6.1 | 1.2 ± 1.2 | 0.0 ± 0.0 |

Example 5

Examination of Culture Solution Composition

Using culture solutions having concentrations (compositions) in the range shown in Table 2, ovulated eggs obtained after culturing for 1 hour after fragmentation and microplate distribution treatment immediately after ovarian removal were artificially inseminated. First, as a result of testing at concentrations of 50%, 100%, 150%, or 200%, fertilized eggs and larvae were obtained at all concentrations.

Furthermore, as a result of conducting the same test at concentrations from 100% to 175% using separate individuals, good culturing results were obtained at concentrations from 100% to 150% (Table 3).

TABLE 2

| Concentration (%) | Na (mM) | K (mM) | Ca (mM) | Mg (mM) |
| --- | --- | --- | --- | --- |
| 50 | 62.05 | 2.55 | 0.80 | 0.50 |
| 100 | 124.10 | 5.10 | 1.60 | 1.00 |
| 125 | 155.13 | 6.38 | 2.00 | 1.25 |
| 150 | 186.15 | 7.65 | 2.40 | 1.50 |

TABLE 2-continued

| Concentration (%) | Na (mM) | K (mM) | Ca (mM) | Mg (mM) |
|---|---|---|---|---|
| 175 | 217.18 | 8.93 | 2.80 | 1.75 |
| 200 | 248.20 | 10.20 | 3.20 | 2.00 |

TABLE 3

| | Concentration (%) | | | |
|---|---|---|---|---|
| | 100 | 125 | 150 | 175 |
| Ovulation rate | 92.2 ± 2.3 | 85.9 ± 3.3 | 71.3 ± 5.8 | 52.7 ± 4.7 |
| Flotation rate (%) | 96.3 ± 1.0 | 94.3 ± 3.0 | 97.7 ± 1.6 | 91.6 ± 3.6 |
| Fertilization rate (%) | 75.7 ± 3.4 | 86.8 ± 1.8 | 73.1 ± 4.1 | 36.7 ± 6.2 |
| Hatching rate (%) | 63.5 ± 3.9 | 70.7 ± 3.7 | 80.6 ± 4.6 | 43.2 ± 7.8 |

Example 6

Adjustment of Culture Solution Matching Metal Ion Composition of Tuna Blood Serum Blood serum was collected from five female fish, and the concentrations of sodium ions and potassium ions were measured by the ion selective electrode method. Additionally, the concentrations of calcium ions and magnesium ions were measured by atomic absorption method.

The results showed that the collected blood serum had the composition shown in Table 4. To match this metal ion composition, a culture solution having a composition containing 193.6 mM of sodium chloride, 7.8 mM of potassium chloride, 3.8 mM of calcium chloride, and 1.1 mM of magnesium sulfate was prepared. To this solution, 5.6 mM of glucose, antibiotics (100 mg/L of streptomycin sulfate, 50 mg/L of kanamycin sulfate, and 70 mg/L of benzylpenicillin potassium) were added, and 10 mM of Epps, and the pH was adjusted to 8.0.

TABLE 4

| Na (mM) | K (mM) | Ca (mM) | Mg (mM) |
|---|---|---|---|
| 193.60 ± 0.51 | 7.78 ± 0.31 | 3.78 ± 0.10 | 1.12 ± 0.01 |

Effect of Culture Solution Matching Metal Ion Composition of Tuna Blood Serum

A standard culture solution section using the culture solution described in Example 1 and a tuna culture solution section using the above culture solution matching the metal ion composition of tuna serum were set up. Each underwent fragmentation and microplate distribution treatment immediately after ovarian removal, and was then cultured for 1, 2, 3, and 4 hours, after which they were fertilized, and the ovulation rate, flotation rate, fertilization rate, and hatching rate were calculated. The test was conducted twice using ovaries from two individuals.

The results of the first individual are shown in FIGS. 8 to 11.

Figure 9:
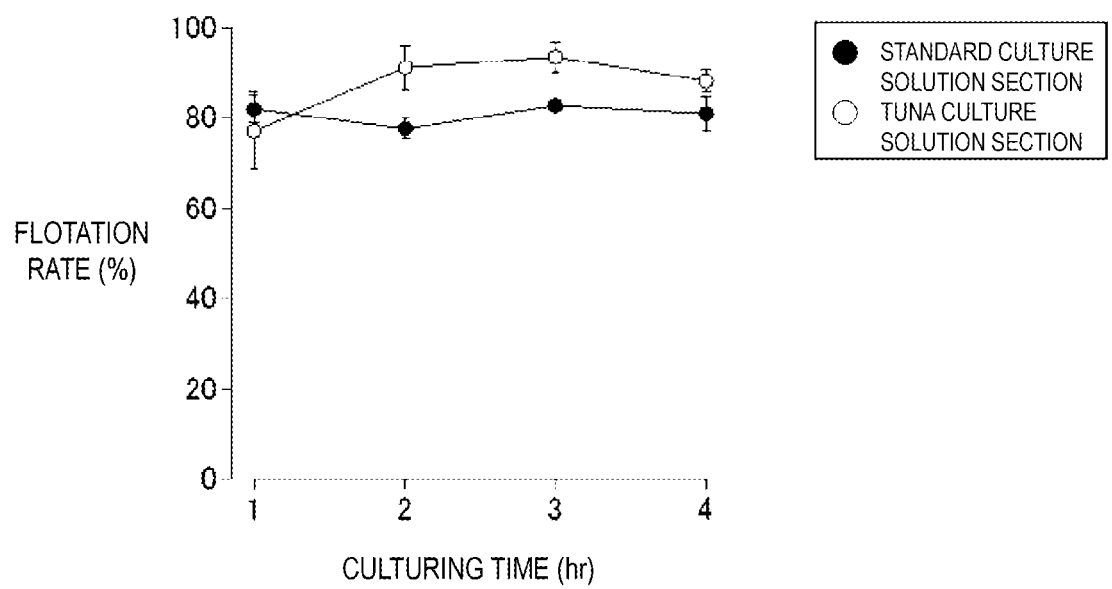
FIG. 9 is a graph showing flotation rate versus culturing time of the standard culture solution section in which the culture solution described in Example 1 is used in a test using ovaries of a first individual, or a tuna culture solution section in which a culture solution matching the metal ion composition of tuna blood serum is used. In the graph, the asterisks indicate a significant difference relative to the standard culture solution section, wherein * means $P<0.05$,  means $P<0.01$, and * means $P<0.001$.
Figure 10:
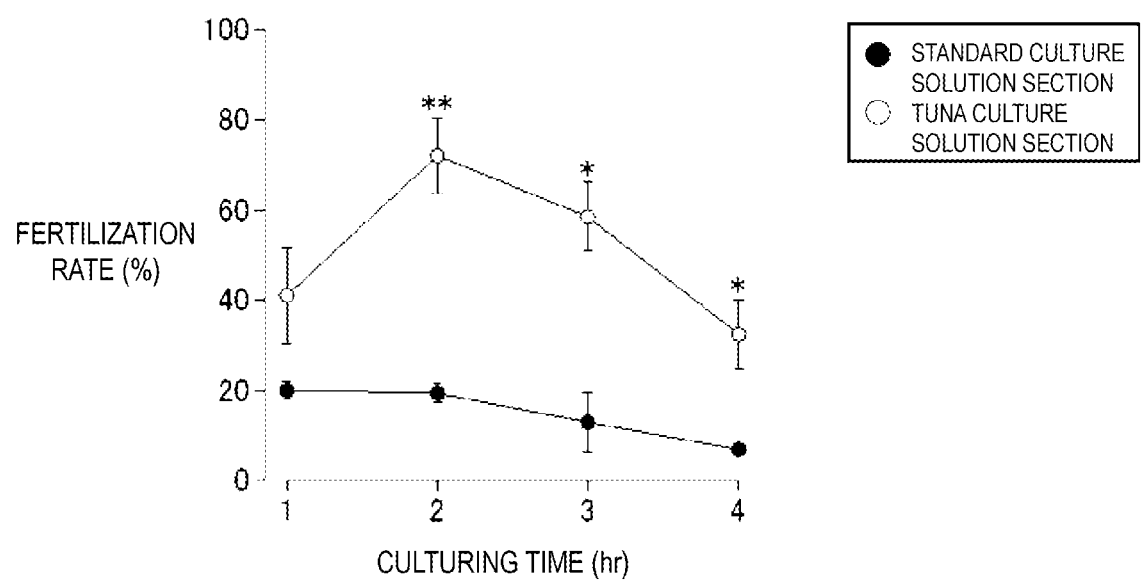
FIG. 10 is a graph showing fertilization rate versus culturing time of the standard culture solution section in which the culture solution described in Example 1 is used in a test using ovaries of a first individual, or a tuna culture solution section in which a culture solution matching the metal ion composition of tuna blood serum is used. In the graph, the asterisks indicate a significant difference relative to the standard culture solution section, wherein * means $P<0.05$,  means $P<0.01$, and * means $P<0.001$.
Figure 11:
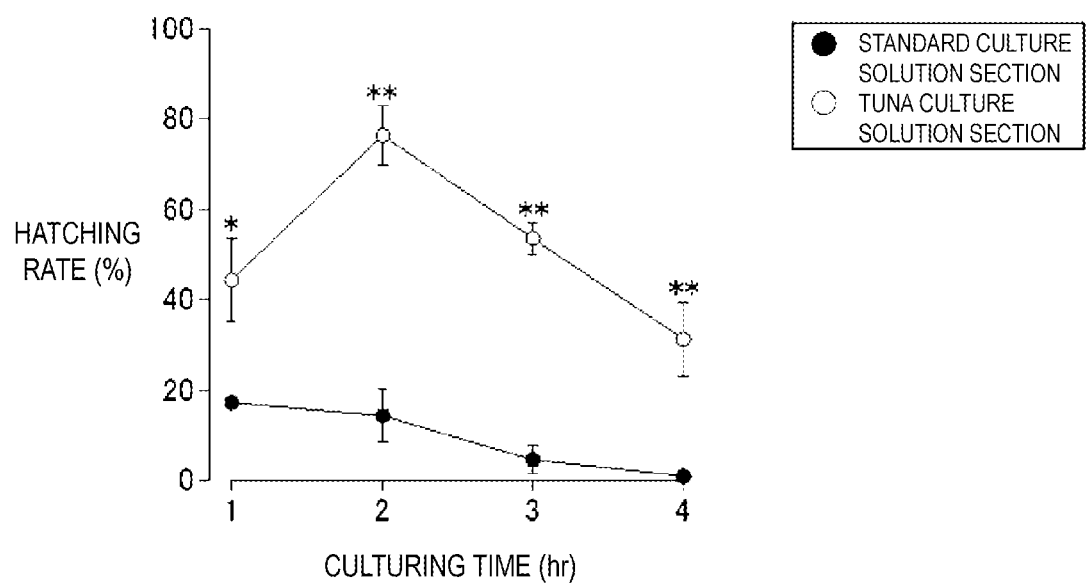
FIG. 11 is a graph showing hatching rate versus culturing time of the standard culture solution section in which the culture solution described in Example 1 is used in a test using ovaries of a first individual, or a tuna culture solution section in which a culture solution matching the metal ion composition of tuna blood serum is used. In the graph, the asterisks indicate a significant difference relative to the standard culture solution section, wherein * means $P<0.05$,  means $P<0.01$, and * means $P<0.001$.
Figure 12:
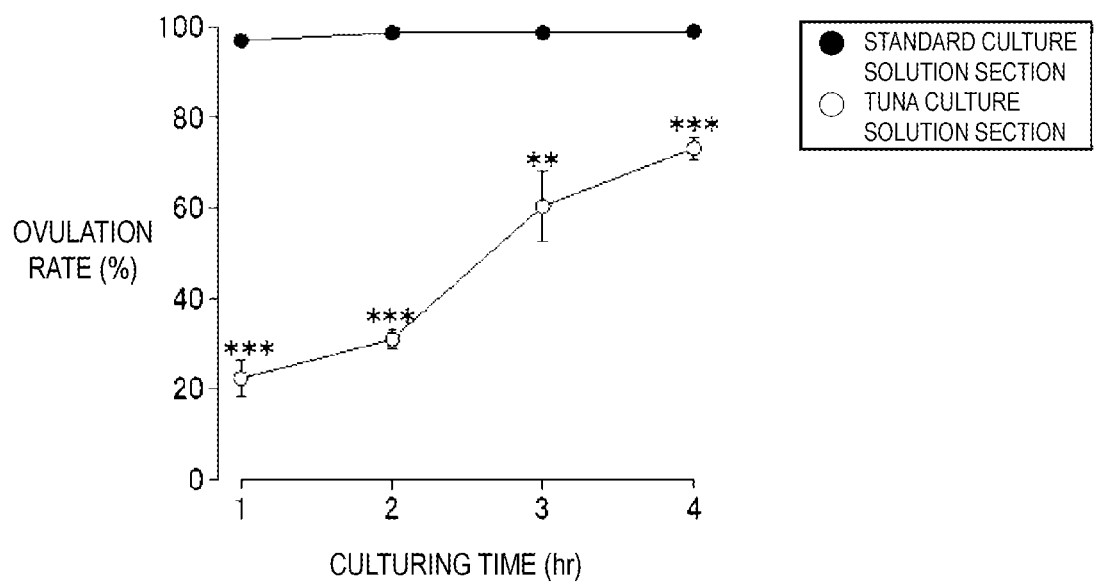
FIG. 12 is a graph showing ovulation rate versus culturing time of the standard culture solution section in which the culture solution described in Example 1 is used in a test using ovaries of a second individual, or a tuna culture solution section in which a culture solution matching the metal ion composition of tuna blood serum is used. In the graph, the asterisks indicate a significant difference relative to the standard culture solution section, wherein * means $P<0.05$,  means $P<0.01$, and * means $P<0.001$.
Figure 13:
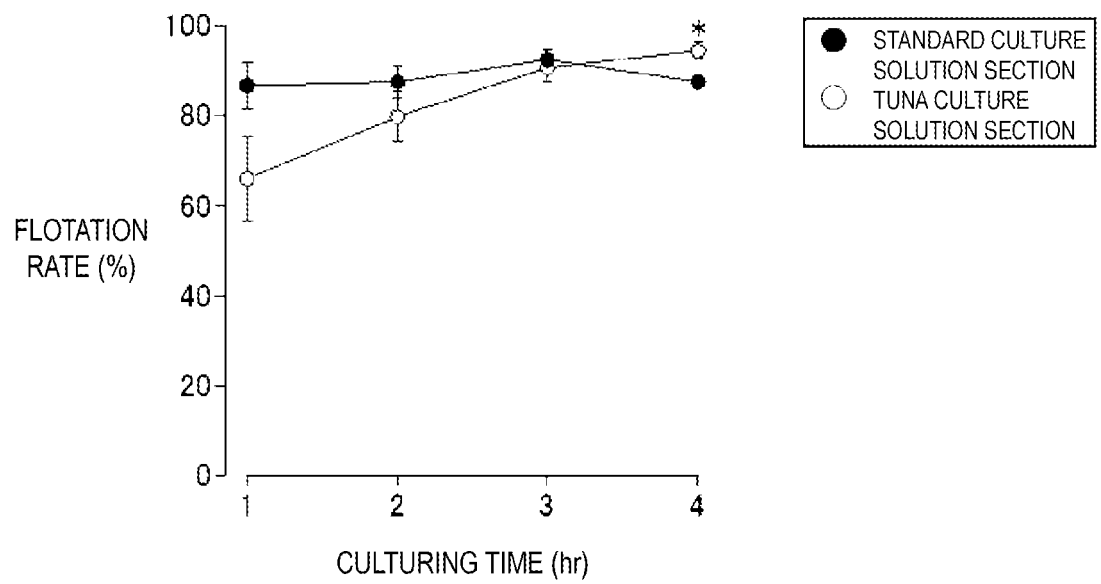
FIG. 13 is a graph showing flotation rate versus culturing time of the standard culture solution section in which the culture solution described in Example 1 is used in a test using ovaries of a second individual, or a tuna culture solution section in which a culture solution matching the metal ion composition of tuna blood serum is used. In the graph, the asterisks indicate a significant difference relative to the standard culture solution section, wherein * means $P<0.05$,  means $P<0.01$, and * means $P<0.001$.
Figure 14:
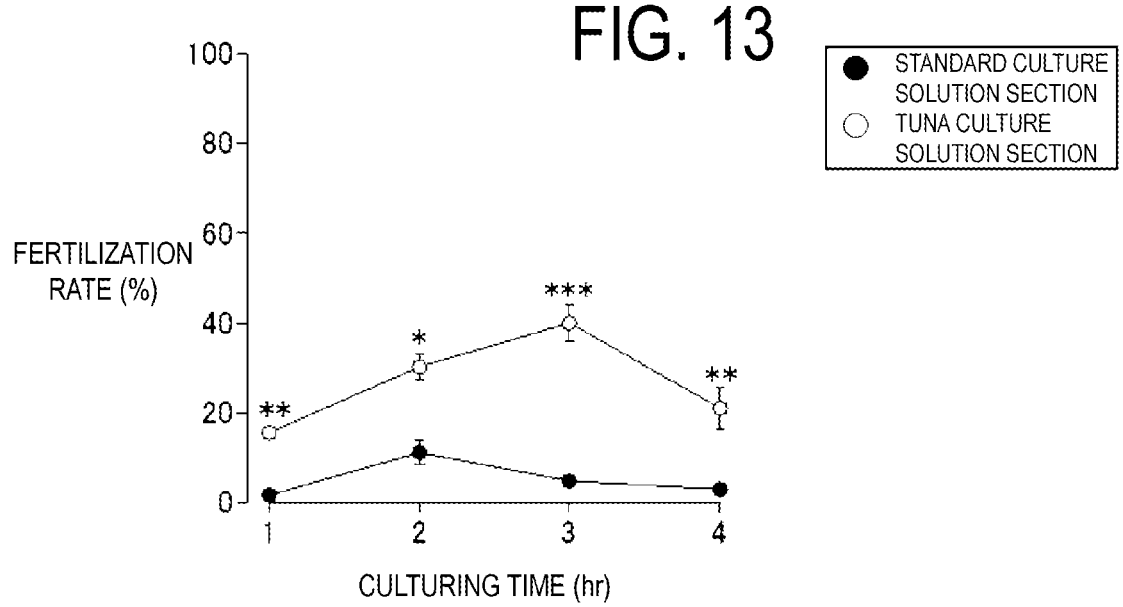
FIG. 14 is a graph showing fertilization rate versus culturing time of the standard culture solution section in which the culture solution described in Example 1 is used in a test using ovaries of a second individual, or a tuna culture solution section in which a culture solution matching the metal ion composition of tuna blood serum is used. In the graph, the asterisks indicate a significant difference relative to the standard culture solution section, wherein * means $P<0.05$,  means $P<0.01$, and * means $P<0.001$.
Figure 15:
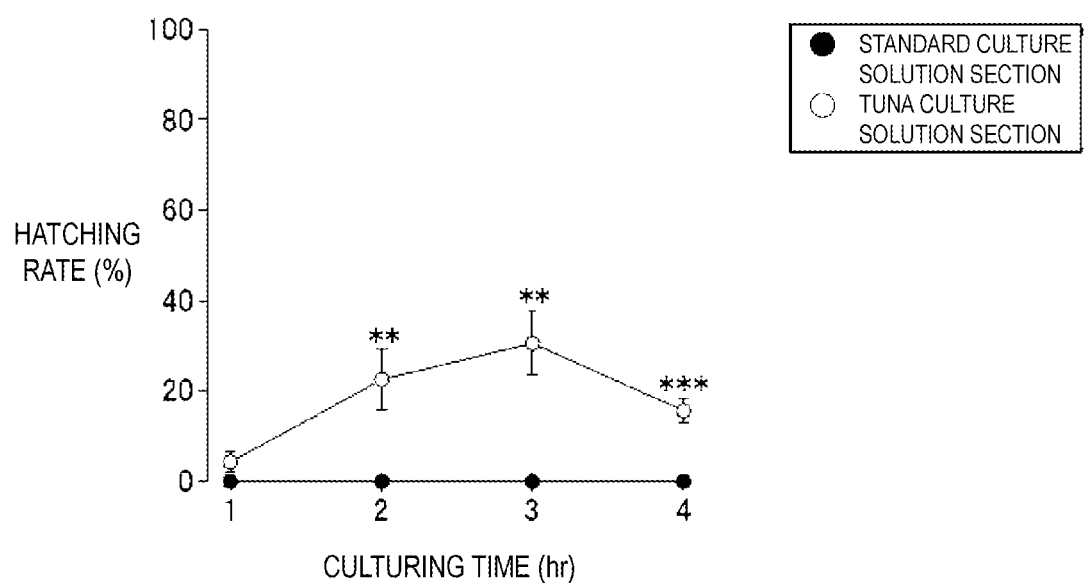
FIG. 15 is a graph showing hatching rate versus culturing time of the standard culture solution section in which the culture solution described in Example 1 is used in a test using ovaries of a second individual, or a tuna culture solution section in which a culture solution matching the metal ion composition of tuna blood serum is used. In the graph, the asterisks indicate a significant difference relative to the standard culture solution section, wherein * means $P<0.05$,  means $P<0.01$, and * means $P<0.001$.

As shown in FIG. 8, the ovulation rate of the standard culture solution section in the first individual reached substantially 100% starting at 1 hour of culturing. In contrast, the ovulation rate of the tuna culture solution section at 1 hour of culturing was low, and then rose with culturing time. No difference in flotation rate was seen between the two sections (FIG. 9). The fertilization rate in the tuna culture solution section was higher than that of the standard culture solution section starting at 2 hours of culturing (FIG. 10). The hatching rate exhibited higher values in the tuna culture solution section than in the standard culture solution section at all culturing times (FIG. 11).

The results of the second individual are shown in FIGS. 12 to 15.

Nearly the same results were seen in the second individual, but the fertilization rate was very low in the standard culture solution section, and the hatching rate was 0% at all culturing times.

The above results demonstrate that when a culture solution that matches the metal ion composition of tuna blood serum is used, the fertilization and hatching results are improved compared to the standard culture solution. Additionally, it was found that hatched larvae were obtained even in cases where it seemed there was no hatching at all. On the other hand, the progression of ovulation was slower than previously seen, but it was ascertained that a certain number of ovulated eggs were obtained by extending culturing time.

INDUSTRIAL APPLICABILITY

The present invention relates to a method of maintaining the ovaries of marine fish, and a method of obtaining fertilized egg. According to the present invention, removed ovaries of marine fish can be easily maintained, fertilized eggs can be easily obtained, and seed can be efficiently produced.

The invention claimed is:

1. A method of maintaining ovaries of marine fish, the method comprising:
   removing ovaries from marine fish, wherein the ovaries comprise oocytes,
   fragmenting the ovaries and conducting microplane distribution treatment immediately after the removing the ovaries from the marine fish, and
   culturing the fragmented and microplane distribution treated ovaries in a culture solution,
   wherein a pH of the cultured solution is adjusted to be from +0.3 to −0.3, relative to a. pH of an ovarian cavity fluid of the marine fish from which the ovaries have been removed.

2. The method according to claim 1, wherein eggs contained in the ovaries are maintained in a fertilizable state.

3. The method according to claim 1, wherein an osmotic pressure of the culture solution is from 100 mOsm/kg to 6000 mOsm/kg.

4. The method according to claim 1, wherein the culture solution comprises at least one selected from the group consisting of a sodium ion, potassium ion, calcium ion, and magnesium ion.

5. The method according to claim 4, wherein a sodium ion concentration of the culture solution is from 120 mM to 250 mM.

6. The method according to claim 4, wherein a potassium ion concentration of the culture solution is from 5 mM to 10 mM.

7. The method according to claim 4, wherein a calcium ion concentration of the culture solution is to 1.5 mM to 5.0 mM.

8. The method according to claim 4, wherein a magnesium ion concentration of the culture solution is from 1.0 mM to 2.0 mM.

9. The method according to claim 1, wherein the culture solution comprises at least one of selected from the group consisting of a chloride ion and sulfate ion.

10. The method according to claim 1, wherein the culture solution comprises at least one selected from the group consisting of glucose, galactose, fructose, and sucrose.

11. The method according to claim 1, wherein the culture solution comprises an antibiotic.

12. The method according to claim 1, wherein the marine fish is a farmed fish.

13. The method according to claim 1, wherein the marine fish is fish caught by fishing.

14. The method according to claim 1, wherein the marine fish is a fish of the Scombridae family.

15. A method of producing eggs of marine fish in vitro, the method comprising obtaining eggs by causing ovaries cultured by the method of claim 1 to ovulate.

16. A method of producing fertilized eggs of marine fish, the method comprising cross-fertilizing eggs obtained by the method of claim 15 and sperm, thereby obtaining fertilized eggs.

17. Eggs of marine fish, the eggs being obtained by method of claim 15.

18. Fertilized eggs of marine fish, the eggs being obtained by the method of claim 16.

19. A method of rearing marine fish, the method comprising rearing larvae hatched from fertilized eggs obtained by the method of claim 16 to young fry, immature fish, or adult fish.

20. A method of producing farmed marine fish, the method comprising rearing larvae hatched from fertilized eggs obtained by the method of claim 16 to young fry, immature fish, or adult fish.

21. The method according to claim 4, wherein molar concentrations of sodium ions, potassium ions, calcium ions, and magnesium ions in the culture solution is from ¼ to 4 times of molar concentrations of sodium ions, potassium ions, calcium ions, and magnesium ions in blood serum of the marine fish from which the ovaries have been removed.

22. The method according to claim 4, wherein a pH of the cultured solution is adjusted to be from +0.1 to −0.1, relative to a pH of an ovarian cavity fluid of the marine fish from which the ovaries have been removed.

* * * * *